(12) United States Patent
Kornecki et al.

(10) Patent No.: US 6,699,688 B1
(45) Date of Patent: Mar. 2, 2004

(54) HUMAN PLATELET F11 RECEPTOR

(75) Inventors: Elizabeth Kornecki, Staten Island, NY (US); Malgorzata B. Sobocka, Brooklyn, NY (US)

(73) Assignee: The Research Foundation of the State University of New York, Albany, NY (US)

( * ) Notice: Subject to any disclaimer, the term of this patent is extended or adjusted under 35 U.S.C. 154(b) by 0 days.

(21) Appl. No.: 09/397,243

(22) Filed: Sep. 16, 1999

Related U.S. Application Data

(60) Provisional application No. 60/100,638, filed on Sep. 16, 1998.

(51) Int. Cl.$^7$ .......................... C07K 1/00; C07H 21/04; C12N 1/20; C12P 21/06; G01N 33/566
(52) U.S. Cl. .................. 435/69.1; 435/6; 435/252.3; 435/320.1; 536/23.5; 530/350; 530/388.22; 514/2; 514/8
(58) Field of Search ........................... 530/350, 388.22; 536/23.5; 514/2, 8; 435/6, 69.1, 252.3, 320.1

(56) References Cited

U.S. PATENT DOCUMENTS 5,665,701 A * 9/1997 Kornecki ................. 514/8

OTHER PUBLICATIONS

Bowie et al., Science 247:1306–1310, 1990.*
Wells Biochemistry 29:8509–8517, 1990.*
Ngo et al., The Protein Folding Problem and Tertiary Structure, pp 492–495, 1994.*
GenBank accession No. AA101561, Oct. 1996.*
SIGMA Product Catalogue, p. 743, 1992.*
Bachelot et al., Cellular Signalling, 3(6):537–546 (1991).
Kornecki et al., Haematologia, 17(3):387–398 (1984).
Kornecki et al., Thrombosis Research, 34:35–49 (1984).
Kornecki et al., The Journal of Biological Chemistry, 265(17):10042–10048 (1990).
Kornecki et al., The Journal of Biological Chemistry, 258(15):9349–9356 (1983).
Naik et al. Biochem. J., 310:155–162 (1995).
Slupsky et al., The Journal of Biological Chemistry, 264(21):12289–12293 (1989).
Wang, et al., Biochem. J., 311:401–406 (1995).

* cited by examiner

*Primary Examiner*—Yvonne Eyler
*Assistant Examiner*—Michael Brannock
(74) *Attorney, Agent, or Firm*—Rogalsky & Weyand, LLP

(57) ABSTRACT

The present invention is directed to isolated nucleic acid molecules encoding human platelet F11 receptors. Expression vectors and host cells comprising the nucleic acid molecules are also provided, as well as methods for increasing or decreasing the expression of the human platelet F11 receptor in host cells. The invention further provides a method of screening a substance for the ability of the substance to modify human platelet F11 receptor function, and a method for isolating other human platelet F11 receptor molecules. DNA oligomers capable of hybridizing to the nucleic acid molecule encoding the human platelet F11 receptor are provided, which can be used to detect human platelet F11 receptor in a sample.

11 Claims, 10 Drawing Sheets

```
SEQ I.D. NO: 1:
     AGTGGCCTGA TCGCGATGGG GACAAAGGCG CAAGTCGAGA GGAAACTGTT GTGCCTCTTC ATATTGGCGA   70
SEQ I.D. NO: 3:      M  G   T  K  A   Q  V  E  R   K  L  L   C  L  F   I  L  A  I   19
     TCCTGTTGTG CTCCCTGGCA TTGGGCAGTG TTACAGTGCA CTCTTCTGAA CCTGAAGTCA GAATTCCTGA  140
      L  L  C   S  L  A   L  G  S  V   T  V  H   S  S  E   P  E  V  R   I  P  E   42
     GAATAATCCT GTGAAGTTGT CCTGTGCCTA CTCGGGCTTT TCTTCTCCCC GTGTGGAGTG GAAGTTTGAC  210
      N  N  P   V  K  L  S   C  A  Y   S  G  F   S  S  P  R   V  E  W   K  F  D   65
     CAAGGAGACA CCACCAGACT CGTTTGCTAT AATAACAAGA TCACAGCTTC CTATGAGGAC CGGGTGACCT  280
      Q  G  D  T   T  R  L   V  C  Y   N  N  K  I   T  A  S   Y  E  D   R  V  T  F   89
     TCTTGCCAAC TGGTATCACC TTCAAGTCCG TGACACGGGA AGACACTGGG ACATACACTT GTATGGTCTC  350
       L  P  T   G  I  T   F  K  S  V   T  R  E   D  T  G   T  Y  T   C  M  V  S   112
     TGAGGAAGGC GGCAACAGCT ATGGGGAGGT CAAGGTCAAG CTCATCGTGC TTGTGCCTCC ATCCAAGCCT  420
      E  E  G   G  N  S  Y   G  E  V   K  V  K  L  I  V  L   V  P  P   S  K  P    135
     ACAGTTAACA TCCCCTCCTC TGCCACCATT GGGAACCGGG CACTGCTGAC ATGCTCAGAA CAAGATGGTT  490
      T  V  N  I   P  S  S   A  T  I   G  N  R  A   V  L  T   C  S  E   Q  D  G  S  159
     CCCCCACCTTC TGAATACACC TGGTTCAAAG ATGGGATAGT GATGCCTACG AATCCCAAAA GCACCCGTGC  560
       P  P  S   E  Y  T   W  F  K  D   G  I  V   M  P  T   N  P  K  S   T  R  A   182
     CTTCAGCAAC TCTTCCTATG TCCTGAATCC CACAACAGGA GAGCTGGTCT TTGATCCCCT GTCAGCCTCT  630
      F  S  N   S  S  Y  V   L  N  P   T  T  G   E  L  V  F   D  P  L   S  A  S    205
     GATACTGGAG AATACAGCTG TGAGGCACGG AATGGGTATG GACACCCAT GACTTCAAAT GCTGTGCGCA   700
      D  T  G  E   Y  S  C   E  A  R   N  G  Y  G   T  P  M   T  S  N   A  V  R  M  229
     TGGAAGCTGT GGAGCGGAAT GTGGGGGTCA TCGTGGCAGC CGTCCTTGTA ACCCTGATTC TCCTGGGAAT  770
       E  A  V   E  R  N   V  G  V  I   V  A  A   V  L  V   T  L  I  L   L  G  I   252
     CTTGGTTTTT GGCATCTGGT TTGCCTATAG CCGAGGCCAC TTTGACAGAA CAAAGAAAGG GACTTCGAGT  840
       L  V  F   G  I  W  F   A  Y  S   R  G  H   F  D  R   T  K  K  G   T  S  S   275
     AAGAAGGTGA TTTACAGCCA GCCTAGTGCC CGAAGTGAAG GAGAATTCAA ACAGACCTCG TCATTCCTGG  910
       K  K  V   I  Y  S   Q  P  S  A   R  S  E   G  E  F   K  Q  T  S   S  F  L  V  299
     TGTGAGCCTG GTCGGCTCAC CGCCTATCAT CTGCATTTGC CTTACTCAGG TGCTACCGGA CTCTGGCCCC  980
     TGATGTCTGT AGTTTCACAG GATGCCTTAT TTGTCTTCTA CACCCACAG GGCCCCCTAC TTCTTCGGAT  1050
     GTGTTTTTAA TAATGTCAGC TATGTGCCCC ATCCTCCTTC ATGCCCTCCC TCCCTTTCCT ACCACTGCTG  1120
     AGTGGCCTGG AACTTGTTTA AAGTGTTTAT TCCTCATTTC TTTGAGGGAT CAGGAAGGAA TCCTGGGTAT  1190
     GCCATTGACT TCCCTTCTAA GTAGACAGCA AAAATGGCGG GGGTCGCAGG AATCTGCACT CAACTGCCCA  1260
     CCTGGCTGGC AGGGATCTTT GAATAGGTAT CTTGAGCTTG GTTCTGGGCT CTTTCCTTGT GTACTGACGA  1330
     CCAGGGCCAG CTGTTCTAGA GCGGGAATTA GAGGCTAGAG CGGCTGAAAT GGTTGTTTGG TGATGACACT  1400
     GGGGTCCTTC CATCTCTGGG GCCCACTCTC TTCTGTCTTC CCATGGGAAG TGCCACTGGG ATCCCTCTGC  1470
     CCTGTCCTCC TGAATACAAG CTGACTGACA TTGACTGTGT CTGTGGAAAA TGGGAGCTCT TGTTGTGGAG  1540
     AGCATAGTAA ATTTTCAGAG AACTTGAAGC CAAAAGGATT TAAAACCGCT GCTCTAAAGA AAAGAAAACT  1610
     GGAGGCTGGG CGCAGTGGCT CACGCCTATA ATCCCAGAGG CTGAGGCAGG CGGATCACCT GAGGTCAGGA  1680
     GTTCAGGATC AGCCTGACCA ACATGGAGAA ACCCTGCTGG AAATACAAAG TTAGCCAGGC ATGGTGGTGC  1750
     ATGCCTGTAG TCCCAGCTGC TCAGGAGCCT GGCAACAAGA GCAAAACTCC AGCTCAAAAA AAAAAAAAA  1820
AA  1822
```

*FIG. 2*

1. Amino acids 41-116 (25% identity to C2 profile)

```
                 ---b---      ---c---                            ---d--- --e--      ---f---
profile  LEGQSVTLTCPasgDPVPNITWLKd..........gkPLPe...srlvaSGSTLTIKNVSlEDSGLYTCVARNSVG  SEQ I.D. NO: 8
41-116   PENNPVKLSCAYSGFSSPRVEWKFDQGDTTRLVCYNNKITASYEDRVTFLPTGITFKSVTREDTGTYTCMVSEEGG  SEQ I.D. NO: 9
```

FIG. 4A

2. Amino acids 144-219 (30% identity to C2 profile)

```
                ---b---       ---c---                            ---d--- --e--     ---f---
profile  LEGQSVTLTCPa.sgDPVPNITWLKdgkPLPe...........s.rlvaSGSTLTIKNVSlEDSGLYTCVARNSVG  SEQ I.D. NO: 10
144-219  TIGNRAVLTCSEQDGSPPSEYTWFKDGIVMPTNPKSTRAFSNSSYVLNPTTGELVFDPLSASDTGEYSCEARNGYG  SEQ I.D. NO: 11
```

```
SEQ
I.D.                                                                                              ----C2/V--------------
NO:          1                    |20                   |40                   |60
     3 FAM   MGTKAQVERKLLCLFLIAILLCSLALGSVTVHSSEPEVRIPENNPVKLSCAYSGFSSPR---VEW-KFDQGDTTRLVCY--NNKI
    12 JAM   MGTEGKAGRKLLFLFTSMI-LGSLVQGKGSVYTAQSDVQVPENESIKLTCTYSGFSSPR---VEW-KFVQGSTTALVCY--NSQI
    13 A33   MVGK--MWPVLWTL----CAVRVTVDA-ISVETPQDVLRASQGKSVTLPCTYHTSTSSREGLIQWDKTHTE---RVVIWPFSNKN

|80                    |100                   |120                   |140
       FAM   TAS---YEDRVTFL------PTGITFKSVTREDTGTYTCMVSEEGG-NSYGEVKVKLIVLVPPSKPTVNIPSSATIGNRAVLTCS
       JAM   TAP---YADRVTFS------SSGITFSSVTRKDNGEYTCMVSEEGG-QNYGEVSIHLTVLVPPSKPTISVPSSVTIGNRAVLTCS
       A33   YIHGELYKNRVSISNNAEQSDASITIDQLTMADNGTYECSVSLMSDLEGNTKSRVRLLVLVPPSKPECGIEGETIIGNNIQLTCQ

----------C2-----------
                            |160                   |180                   |200                   |220
       FAM   EQDGSPPSEYTWFKDGIVMPTNP-KSTRAFSNSSYVLNPTTGELVFDPLSASD-TGEYSCEARNGYGTPMTSNAVRMEAVERNVGV
       JAM   EHDGSPPSEYSWFKDGISMLTADAKKTRAFMNSSFTIDPKSGDLIFDPVTAFD-SGEYYCQAQNGYGTAMRSEAAHMDAVELNVGG
       A33   SKEGSPTPQYSWKRYNILNQEQP-LAQPASGQPVSLKNIST-------------DTSGYYICTSSNEEGTQFCNITVAVRSPSMNVAL

-----TM-------
                            |240                   |260                   |280
       FAM   IVA-AVLV--TLILLGILVFGIWFAYSRGHFDRT--KKGTSS-KKVIYSQP-------SARSEGEFK-----QTSSFLV
       JAM   IVA-AVLV--TLILLGLLIFGVWFAYSRGYFETT--KKGTAPGKKVIYSQP-------STRSEGEFK-----QTSSFLV
       A33   YVGIAVGVVAALIIGIIIYCCCC---RGKDDNTEDKEDARP-NREAYEEPPEQLRELSREREEDDYRQEEQRSTGRESPDHLDQ
```

FIG. 6

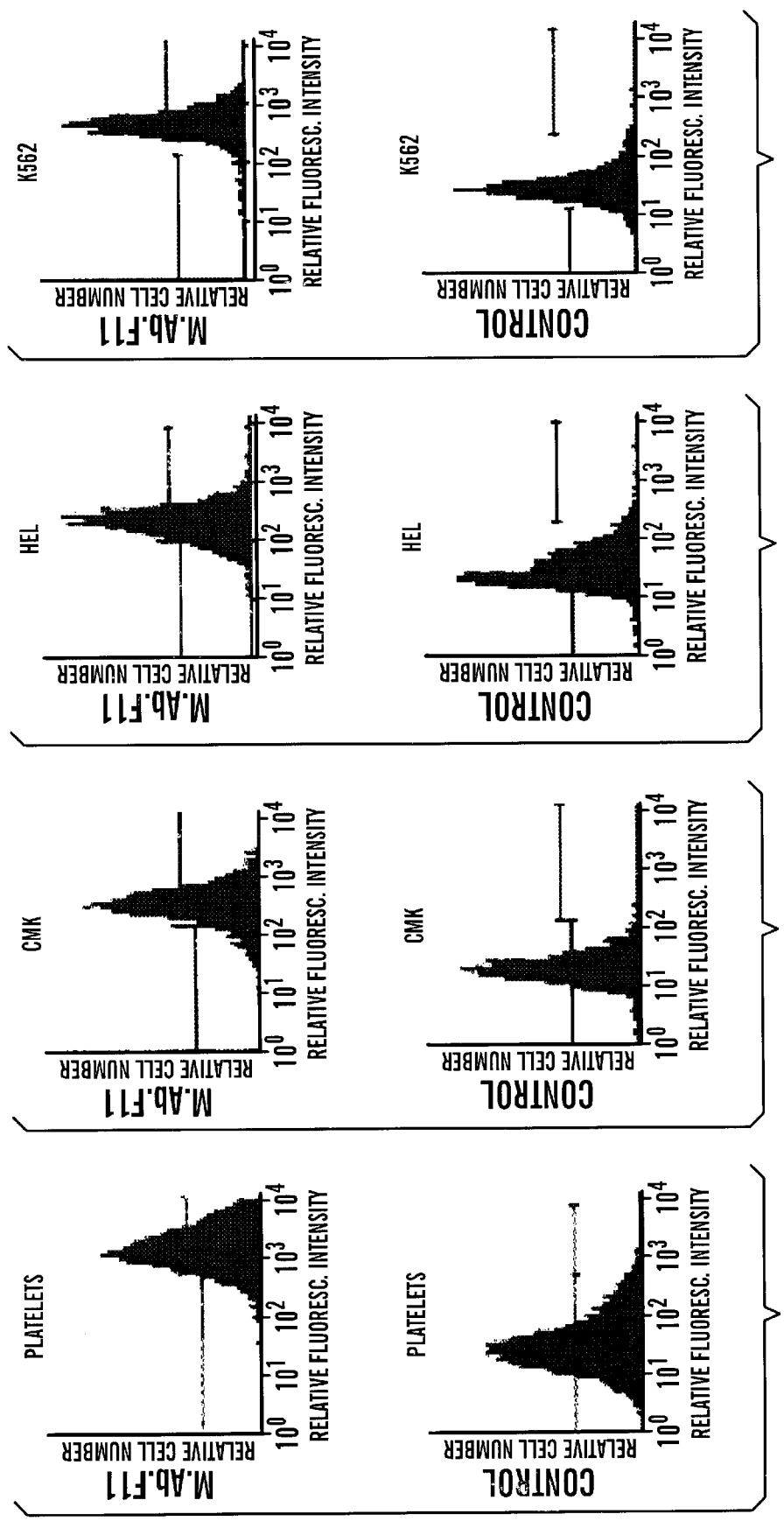

HUMAN PLATELET F11 RECEPTOR

This application claims priority of U.S. Provisional Patent Application No. 60/100,638, filed Sep. 16, 1998.

FIELD OF THE INVENTION

The subject invention is directed generally to the human platelet F11 receptor, and more particularly to nucleic acid molecules encoding the human platelet F11 receptor and uses thereof.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

The significant role of platelet activation in hemostasis is well-documented. Platelet activation is necessary for platelet aggregation and secretion, and is initiated by the binding of agonist to receptors at the platelet surface. Over the last ten years, several laboratories have developed monoclonal antibodies to platelet membrane glycoproteins. These platelet membrane glycoproteins can serve as agonist receptors on the platelet membrane. The antibodies to these glycoproteins have been of great value in studies designed to elucidate the structure and function of these glycoproteins.

Most of the success in raising monoclonal antibodies to platelet receptors was in studies on the integrin cohesion receptor IIb/IIIa (Coller et al., 1983; Kornecki et al., 1984) and the adhesion receptor Ib/IX (Coller et al., 1983; Handa et al., 1986). Functional antibodies that inhibit the action of these receptors provided a large body of new information and have led to direct conclusions about the functions of these glycoprotein receptors. Such inhibitory antibodies were also shown to have potential in vivo therapeutic use (Coller et al., 1986; Peters et al., 1986).

Some of these antibodies that serve as agonists, binding to the receptors at the platelet surface and thereby activating the platelets, have been identified. Several laboratories have developed or identified such "activator" antibodies that appear to react with platelet membrane protein components of 21–24 kD. The first report of a monoclonal antibody which served as an agonist and induced platelet aggregation was published by Boucheix et al. in 1983. This monoclonal antibody immunoprecipitated a platelet protein with apparent molecular weight (M.W.) of 24 kD under both reduced and non-reduced conditions. The addition of Fab fragments of this antibody to platelets resulted in the inhibition of platelet aggregation induced by various agonists. The platelet antigen recognized by this antibody was identical to the leukemia-associated antigen, p24, found in common acute lymphoblastic leukemia cells and neuroblastoma cells (Kersey et al., 1981; Jones et al., 1982; Komada et al., 1983).

Thiagarajan et al. (1983) reported that platelet aggregation could be induced by another monoclonal antibody. This antibody was found to be directed against a 21 kD protein present in both normal and Glanzmann's thrombasthenic platelets.

Gorman et al. (1985) have described several monoclonal antibodies which induce platelet aggregation. All of these antibodies immunoprecipitated a 24 kD platelet protein in both the reduced and non-reduced states. The Fab fragments of these antibodies were found to augment the aggregation of platelets by adenosine diphosphate (ADP).

Higashihara et al. (1985) also described a monoclonal antibody which induced platelet aggregation and secretion by interaction with a protein of 24 kD. Preincubation of platelets with this antibody inhibited ristocetin-induced agglutination. It is known that these antibodies are directed against the p24/CD9 protein on the platelet surface. The CD9 antigen has been cloned and sequenced (Boucheix et al., 1991; Lanza et al., 1991), and CD9 antibodies have been shown to induce platelet aggregation mediated by the FcγRII receptor (CD32 molecule) (Worthington et al., 1990).

Duncan and Rosse (1986) showed that antibodies to platelet HLA class I antigen (anti-ABH IgG) could activate platelets and induce serotonin release. Similar results were obtained by Cosgrove et al. (1988), who reported that three different anti-HLA Class I monoclonal antibodies and an anti-$β_2$ microglobulin antibody caused platelet aggregation and secretion. Duncan and Rosse (1986) also showed that high concentrations of anti-$PL^{A1}$ antibodies inhibited platelet secretion induced by these antibodies. Ryu et al. (1989) found that high concentrations of PLA1 blocked fibrinogen binding resulting in the blockage of agonist-induced platelet aggregation, whereas low concentrations of anti-$PL^{A1}$ antibodies induced release and aggregation.

Activator monoclonal antibodies directed against GPIIb and GPIIIa have also been reported. A stimulatory monoclonal antibody to the GPIIb/IIIa complex has been described by Modderman et al. (1988) which induces the release of alpha and dense granule contents resulting in platelet aggregation. Morel et al. (1989) have described a monoclonal antibody directed against GPIIb. The F(ab')$_2$ fragments of this antibody did not induce platelet aggregation although they blocked the stimulation of platelets by the intact antibody.

In addition to these antibodies, antibodies of other specificity have been described which activate platelets. Scott et al. (1989) described a monoclonal antibody which stimulates platelet secretion and aggregation and is directed against a platelet membrane glycoprotein of M. W. 67 kD. Recently, Yanabu et al. (1991) detected an autoantibody in a patient with immunothrombocytopenia (ITP), which activated normal platelets by interacting with a 36 kD platelet surface protein.

Kornecki et al. (1990) referred to a monoclonal antibody called M.Ab.F11 which induces vesicular secretion and aggregation in human platelets. U.S. Pat. No. 5,665,701, issued Sep. 9, 1997, of Kornecki et al. (the entire contents of which are incorporated herein by reference) discloses further details of the F11 receptor protein, including partial amino acid sequences. Although the Patent refers to DNA encoding the platelet membrane glycoprotein F11 (column 4, line 10), no nucleotide sequences encoding the protein are provided or described.

The health related significance of these antibodies which can activate human platelets is apparent. Characterization of the antigens which serve as receptors for these antibodies in the activation process is necessary as well as the elucidation of the biochemical pathways triggered by these interactions.

SUMMARY OF THE INVENTION

To this end, the subject invention provides an isolated nucleic acid molecule encoding a human platelet F11 receptor. The invention also provides an antisense nucleic acid molecule complementary to at least a portion of the mRNA encoding the human platelet F11 receptor.

The isolated nucleic acid molecules of the invention can be inserted into suitable expression vectors and/or host cells.

Expression of the nucleic acid molecules encoding the human platelet F11 receptor results in production of human platelet F11 receptor in a host cell. Expression of the antisense nucleic acid molecules in a host cell results in decreased expression of the human platelet F11 receptor.

The invention further provides a ribozyme having a recognition sequence complementary to a portion of mRNA encoding a human platelet F11 receptor. The ribozyme can be introduced into a cell to also achieve decreased expression of human platelet F11 receptor in the cell.

The invention further provides a method of screening a substance for the ability of the substance to modify F11 receptor function, and a method of obtaining DNA encoding a human platelet F11 receptor.

Further provided is an isolated nucleic acid molecule encoding a human platelet F11 receptor, wherein the nucleic acid molecule encodes a first amino acid sequence having at least 90% amino acid identity to a second amino acid sequence. The second amino acid sequence has an amino acid sequence selected from the group consisting of SEQ ID NO:3, amino acid residues 28–299 of SEQ ID NO:3, SEQ ID NO:4, and amino acid residues 28–193 of SEQ ID NO:4.

The invention further provides a DNA oligomer capable of hybridizing to a nucleic acid molecule encoding a human platelet F11 receptor. The DNA oligomer can be used in a method of detecting presence of a human platelet F11 receptor in a sample, which method is also provided by the subject invention.

The subject invention is based on the discovery that a stimulatory monoclonal antibody (termed M.Ab.F11) induces aggregation and granule secretion of human platelets through its specific binding to a platelet membrane glycoprotein duplex of MW 32 and 35 kDa, termed F11 receptor (also referred to as FAM or F11-Adhesion Molecule). Internal amino acid sequences of FAM enabled the cloning of a full-length cDNA. The predicted amino acid sequence revealed that FAM is an integral membrane protein. An extracellular N-terminal region consisting of two Ig-like C2-type domains is followed by a transmembrane domain and a short cytoplasmic tail. FAM is thus a new member of the Ig gene superfamily. FAM showed 69% homology with the murine junctional adhesion molecule (JAM). An immunocytochemical location in the tight junctions of HUVEC cells, similar to that shown by JAM in mouse cells, suggests a role for FAM in cell-cell adhesion in addition to participation in platelet activation. By Western blotting, a number of myeloid and vascular cells were,found to express FAM. The detection of autoantibodies against FAM in the circulation of thrombocytopenic and renal patients indicates that FAM may play a pathophysiological role in clinical disorders involving the activation of platelets in vivo.

BRIEF DESCRIPTION OF THE DRAWINGS

These and other features and advantages of this invention will be evident from the following detailed description of preferred embodiments when read in conjunction with the accompanying drawings in which:

FIG. 2 illustrates the human platelet FAM nucleotide sequence (SEQ ID NO:1) and deduced amino acid sequence (SEQ ID NO:3). The N-terminal amino acid sequence of the mature FAM (SEQ ID NO:5: SVTVHSS-EPEVRIPENNPVKLS) and internal sequences of peptides GluC-(4) (SEQ ID NO:6: WKFDQGDTTRLVCY-NNKITASYEDRVTFLPTGITFKSVTRED) and GluC-(2) (SEQ ID NO:7: KVKLIVLV) are underlined. The start codon is indicated by a double line;

FIGS. 4A and 4B illustrate that FAM is a member of the Ig family. The FAM molecule contains two C2-type Ig domains. These figures show the alignment of the C2-type Ig domain consensus sequence profiles with FAM at amino acid 41–116 of SEQ ID NO:3 (FIG. 4A, SEQ ID NO:9) and with FAM at amino acids 144–219 of SEQ ID NO:3 (FIG. 4B, SEQ ID NO:11). The conserved cysteine residues are boxed;

FIG. 6 illustrates the alignment of the amino acid sequences of the FAM with the Junctional Adhesion molecule (JAM) (Bachelot et al. 1990) and the A33 molecule (Jennings et al. 1990). The C-2/V Ig fold for each protein are indicated by the dashed lines. TM =transmembrane region;

FIGS. 7A–7H illustrate the cellular distribution of FAM as determined by flow cytometry. Each cell type was incubated with M.Ab.F11 (5 mg/ml), followed by the addition of the secondary antibody GAM IgG-FITC. Cells were analyzed by FAC Sort flow cytometry. As controls, cells were incubated with nonimmune mouse IgG, followed by incubation with the secondary antibody. Cells considered positive for FAM exhibited a mean fluorescence intensity of 40 channels higher than control groups. Each figure is representative of 5 experiments. FIG. 7A=platelets; FIG. 7B=CMK; FIG. 7C=HEL; FIG. 7D=K562; FIG. 7E=erythrocytes; FIG. 7F=lymphocytes; FIG. 7G=HUVEC; FIG. 7H=Eahy 926;

DETAILED DESCRIPTION OF THE INVENTION

Abbreviations Used Herein

Figure 1:
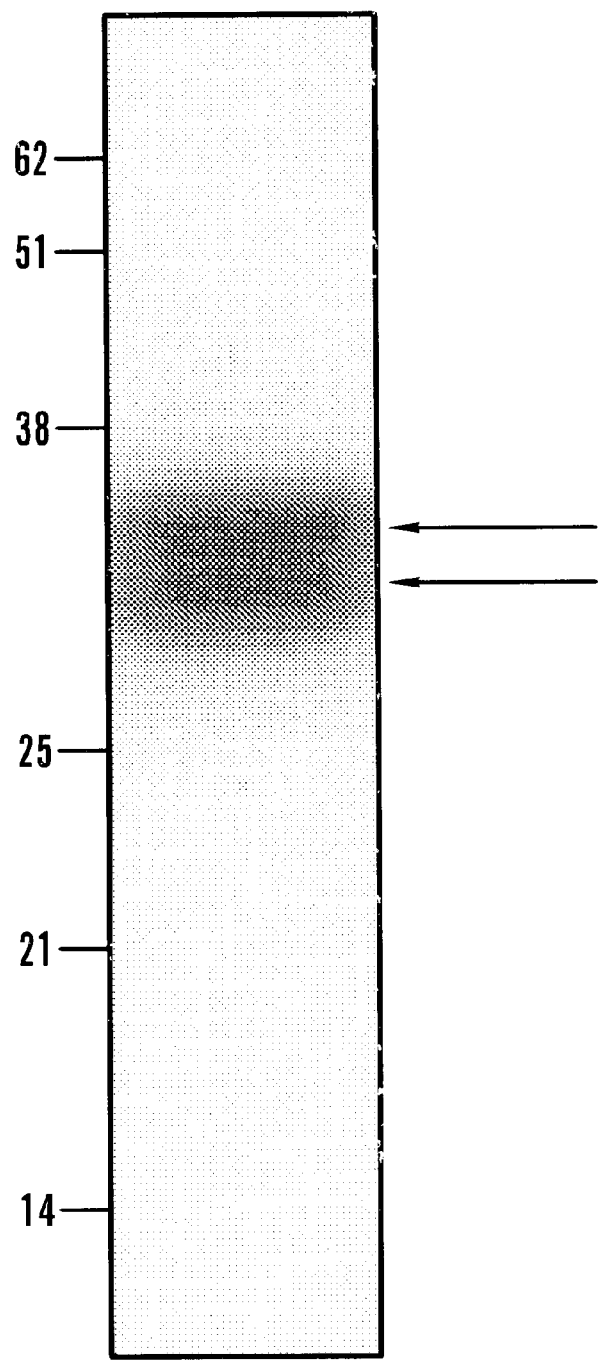
FIG. 1 illustrates the detection of FAM in human platelets by use of a polyclonal antibody directed against the twenty-one amino acid sequence of the terminus of purified FAM. Total platelet proteins, solubilized from approximately $2 \times 10^7$ platelets, were resolved on a 15% SDS-polyacrylamide gel. For immunoblotting, an anti-FAM polyclonal antibody, developed against the N-terminal sequence, was used at a concentration of 20 mg/ml. The arrows point to the 32/35 kDa duplex.

ACD (acid citrate dextrose)
BAEC (bovine aortic endothelial cells)
DMEM (Dubelcco's modified Eagle's medium)
F11R (F11 receptor)
GP (glycoprotein)
HAT (hypoxanthine-aminopterin-thymidine)
HBS (HEPES-buffered saline)
HEL (human erythroleukemic cell line)
HMM (Hidden Markov Model)
HUVEC (human umbilical vein endothelial cells)
ICAM (intercellular adhesion molecule)
IgSF (Immunoglobulin superfamily)
M.Ab. (monoclonal antibody)
MadCAM-1 (mucosal addressin cell adhesion molecule-1)
NCAM (neural cell adhesion molecule)
PDGF (platelet-derived growth factor)
PECAM-1 (platelet endothelial cell adhesion molecule-1)
$PGE_1$ (prostaglandin $E_1$)
RACE (Rapid Amplification of cDNA Ends)
RT-PCR (Reverse Transcriptase-Polymerase Chain Reaction)
SMART (Simple Modular Architecture Research Tool)
VCAM-1 (vascular cell adhesion molecule-1)

Monoclonal antibody M.Ab.F11 (directed to the F11 receptor) has been deposited pursuant to, and in satisfaction of, the requirements of the Budapest Treaty on the International Recognition of the Deposit of Microorganisms for the Purposes of Patent Procedure with the American Type Culture Collection (ATCC), 10801 University Blvd., Manassas, Va. 20110-2209 under ATCC Accession No. HB-11761 on November 10, 1994.

The term "nucleic acid", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA, and nonfunctional DNA or RNA.

"Isolated" nucleic acid refers to nucleic acid which has been separated from an organism in a substantially purified form (i.e. substantially free of other substances originating from that organism), and to synthetic nucleic acid.

By a nucleic acid sequence "homologous to" or "complementary to", it is meant a nucleic acid that selectively hybridizes, duplexes or binds to DNA sequences encoding the F11 receptor (protein) or portions thereof when the DNA sequences encoding the protein are present in a human genomic or cDNA library. A DNA sequence which is similar or complementary to a target sequence can include sequences which are shorter or longer than the target sequence so long as they meet the functional test set forth.

Typically, the hybridization is done in a Southern blot protocol using a 0.2×SSC, 0.1% SDS, 65° C. wash. The term "SSC" refers to a citrate-saline solution of 0.15M sodium chloride and 20 mM sodium citrate. Solutions are often expressed as multiples or fractions of this concentration. For example, 6×SSC refers to a solution having a sodium chloride and sodium citrate concentration of 6 times this amount or 0.9 M sodium chloride and 120 mM sodium citrate. 0.2×SSC refers to a solution 0.2 times the SSC concentration or 0.03M sodium chloride and 4 mM sodium citrate.

The phrase "nucleic acid molecule encoding" refers to a nucleic acid molecule which directs the expression of a specific protein or peptide. The nucleic acid sequences include both the DNA strand sequence that is transcribed into RNA and the RNA sequence that is translated into protein or peptide. The nucleic acid molecule includes both the full length nucleic acid sequences as well as non-full length sequences derived from the full length protein. It being further understood that the sequence includes the degenerate codons of the native sequence or sequences which may be introduced to provide codon preference in a specific host cell.

The term "located upstream" as used herein refers to linkage of a promoter upstream from a nucleic acid (DNA) sequence such that the promoter mediates transcription of the nucleic acid (DNA) sequence.

The term "vector", refers to viral expression systems, autonomous self-replicating circular DNA (plasmids), and includes both expression and nonexpression plasmids. Where a recombinant microorganism or cell is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or the vector may be incorporated within the ost's genome.

The term "plasmid" refers to an autonomous circular DNA molecule capable of replication in a cell, and includes both the expression and nonexpression types. Where a recombinant microorganism or cell is described as hosting an "expression plasmid", this includes latent viral DNA integrated into the host chromosome(s). Where a plasmid is being maintained by a host cell, the plasmid is either being stably replicated by the cell during mitosis as an autonomous structure, or the plasmid is incorporated within the host's genome.

The phrase "heterologous protein" or "recombinantly produced heterologous protein" refers to a peptide or protein of interest produced using cells that do not have an endogenous copy of DNA able to express the peptide or protein of interest. The cells produce the peptide or protein because they have been genetically altered by the introduction of the appropriate nucleic acid sequences. The recombinant peptide or protein will not be found in association with peptides or proteins and other subcellular components normally associated with the cells producing the peptide or protein.

The following terms are used to describe the sequence relationships between two or more nucleic acid molecules or polynucleotides, or between two or more amino acid sequences of peptides or proteins: "reference sequence", "comparison window", "sequence identity", "sequence homology", "percentage of sequence identity", "percentage of sequence homology", "substantial identity", and "substantial homology". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted, for example, by the local homology algorithm of Smith and Waterman (1981), by the homology alignment algorithm of Needleman and Wunsch (1970), by the search for similarity method of Pearson and Lipman (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to nucleic acid molecules or polynucleotides, the terms "substantial identity" or "substantial sequence identity" mean that two nucleic acid sequences, when optimally aligned (see above), share at least 90 percent sequence identity, preferably at least 95 percent sequence identity, more preferably at least 96, 97, 98 or 99 percent sequence identity.

"Percentage nucleotide (or nucleic acid) identity" or "percentage nucleotide (or nucleic acid) sequence identity" refers to a comparison of the nucleotides of two nucleic acid molecules which, when optimally aligned, have approximately the designated percentage of the same nucleotides. For example, "95% nucleotide identity" refers to a comparison of the nucleotides of two nucleic acid molecules which when optimally aligned have 95% nucleotide identity. Preferably, nucleotide positions which are not identical differ by redundant nucleotide substitutions (the nucleotide substitution does not change the amino acid encoded by the particular codon).

As further applied to nucleic acid molecules or polynucleotides, the terms "substantial homology" or "substantial sequence homology" mean that two nucleic acid sequences, when optimally aligned (see above), share at least 90 percent sequence homology, preferably at least 95 percent sequence homology, more preferably at least 96, 97, 98 or 99 percent sequence homology.

"Percentage nucleotide (or nucleic acid) homology" or "percentage nucleotide (or nucleic acid) sequence homology" refers to a comparison of the nucleotides of two nucleic acid molecules which, when optimally aligned, have approximately the designated percentage of the same nucleotides or nucleotides which are not identical but differ by redundant nucleotide substitutions (the nucleotide substitution does not change the amino acid encoded by the particular codon). For example, "95% nucleotide homology" refers to a comparison of the nucleotides of two nucleic acid molecules which when optimally aligned have 95% nucleotide homology.

As applied to polypeptides, the terms "substantial identity" or "substantial sequence identity" mean that two peptide sequences, when optimally aligned, such as by the programs GAP or BESTFIT using default gap, share at least 90 percent sequence identity, preferably at least 95 percent sequence identity, more preferably at least 96, 97, 98 or 99 percent sequence identity.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to affect the properties of a protein. Examples include glutamine for asparagine or glutamic acid for aspartic acid.

As further applied to polypeptides, the terms "substantial homology" or "substantial sequence homology" mean that two peptide sequences, when optimally aligned, such as by the programs GAP or BESTFIT using default gap, share at least 90 percent sequence homology, preferably at least 95 percent sequence homology, more preferably at least 96, 97, 98 or 99 percent sequence homology.

"Percentage amino acid homology" or "percentage amino acid sequence homology" refers to a comparison of the amino acids of two polypeptides which, when optimally aligned, have approximately the designated percentage of the same amino acids or conservatively substituted amino acids. For example, "95% amino acid homology" refers to a comparison of the amino acids of two polypeptides which when optimally aligned have 95% amino acid homology. As used herein, homology refers to identical amino acids or residue positions which are not identical but differ only by conservative amino acid substitutions. For example, the substitution of amino acids having similar chemical properties such as charge or polarity are not likely to affect the properties of a protein. Examples include glutamine for asparagine or glutamic acid for aspartic acid.

The phrase "substantially purified" or "isolated" when referring to a protein (or peptide), means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein (or peptide) which is the predominant species present in a preparation is substantially purified. Generally, a substantially purified or isolated protein (or peptide) will comprise more than 80% of all macromolecular species present in the preparation. Preferably, the protein (or peptide) is purified to represent greater than 90% of all macromolecular species present. More preferably the protein (or peptide) is purified to greater than 95%, and most preferably the protein (or peptide) is purified to essential homogeneity, wherein other macromolecular species are not detected by conventional techniques. A "substantially purified" or "isolated" protein (or peptide) can be separated from an organism, synthetically or chemically produced, or recombinantly produced.

"Biological sample" or "sample" as used herein refers to any sample obtained from a living organism or from an organism that has died. Examples of biological samples include body fluids and tissue specimens.

High stringent hybridization conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide concentration, and the extent of base mismatching, the combination of parameters is more important than the absolute measure of any one. High stringency may be attained, for example, by overnight hybridization at about 68° C. in a 6×SSC solution, washing at room temperature with 6×SSC solution, followed by washing at about 68° C. in a 6×SSC solution then in a 0.633 SSX solution.

Hybridization with moderate stringency may be attained, for example, by: 1) filter pre-hybridizing and hybridizing with a solution of 3×sodium chloride, sodium citrate (SSC), 50% formamide, 0.1M Tris buffer at pH 7.5, 5× Denhardt's solution; 2) pre-hybridization at 37° C. for 4 hours; 3) hybridization at 37° C. with amount of labelled probe equal to 3,000,000 cpm total for 16 hours; 4) wash in 2×SSC and 0.1% SDS solution; 5) wash 4× for 1 minute each at room temperature and 4× at 60° C. for 30 minutes each; and 6) dry and expose to film.

The phrase "selectively hybridizing to" refers to a nucleic acid molecule that hybridizes, duplexes or binds only to a particular target DNA or RNA sequence when the target sequences are present in a preparation of total cellular DNA or RNA. By selectively hybridizing it is meant that a nucleic acid molecule binds to a given target in a manner that is detectable in a different manner from non-target sequence under moderate, or more preferably under high, stringency conditions of hybridization. "Complementary" or "target" nucleic acid sequences refer to those nucleic acid sequences which selectively hybridize to a nucleic acid molecule. Proper annealing conditions depend, for example, upon a nucleic acid molecule's length, base composition, and the number of mismatches and their position on the molecule, and must often be determined empirically. For discussions of nucleic acid molecule (probe) design and annealing conditions, see, for example, Sambrook et al. 1989.

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the peptide/protein to which the relevant sequence listing relates.

The DNA molecules of the subject invention also include DNA molecules coding for protein (receptor) analogs, fragments or derivatives of the protein which differ from naturally-occurring forms (the naturally-occurring protein) in terms of the identity or location of one or more amino acid residues (deletion analogs containing less than all of the residues specified for the protein, substitution analogs wherein one or more residues specified are replaced by other residues, and addition analogs wherein one or more amino acid residues is added to a terminal or medial portion of the protein) and which share the function of the naturally-occurring form. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

As used herein, a "peptide" refers to an amino acid sequence of three to one hundred amino acids, and therefore an isolated peptide that comprises an amino acid sequence is not intended to cover amino acid sequences of greater than 100 amino acids. Preferably, peptides are less than 50 amino acids in length, and more preferably the peptides are five to 20 amino acids in length or 20–40 amino acids in length.

Peptides or proteins can contain any naturally-occurring or non-naturally-occurring amino acids, including the D-form of the amino acids, amino acid derivatives and amino acid mimics, so long as the desired function and activity of the peptide or protein is maintained. The choice of including an (L)- or a (D)-amino acid in the peptides or proteins depends, in part, on the desired characteristics of the peptide or protein. For example, the incorporation of one or more (D)-amino acids can confer increased stability on the peptide or protein and can allow a peptide or protein to remain active in the body for an extended period of time. The incorporation of one or more (D)-amino acids can also increase or decrease the pharmacological activity of the peptide or protein.

The peptides or proteins may also be cyclized, since cyclization may provide the peptides or proteins with superior properties over their linear counterparts.

As used herein, the terms "amino acid mimic" and "mimetic" mean an amino acid analog or non-amino acid moiety that has the same or similar functional characteristic of a given amino acid. For instance, an amino acid mimic of a hydrophobic amino acid is one which is non-polar and retains hydrophobicity, generally by way of containing an aliphatic chemical group. By way of further example, an arginine mimic can be an analog of arginine which contains a side chain having a positive charge at physiological pH, as is characteristic of the guanidinium side chain reactive group of arginine.

In addition, modifications to the peptide backbone and peptide bonds thereof are also encompassed within the scope of amino acid mimic or mimetic. Such modifications can be made to the amino acid, derivative thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al. (1981) and Raucher et al. (1980). An amino acid mimic is, therefor, an organic molecule that retains the similar amino acid pharmacophore groups as is present in the corresponding amino acid and which exhibits substantially the same spatial arrangement between functional groups.

The substitution of amino acids by non-naturally occurring amino acids and amino acid mimics as described above can enhance the overall activity or properties of an individual peptide or protein based on the modifications to the backbone or side chain functionalities. For example, these types of alterations to the specifically described amino acid substituents and exemplified peptides or proteins can enhance the peptide or protein's stability to enzymatic breakdown and increase biological activity. Modifications to the peptide backbone similarly can add stability and enhance activity.

With these definitions in mind, the subject invention provides an isolated nucleic acid molecule encoding a human platelet F11 receptor. The nucleic acid molecule can be deoxyribonucleic acid (DNA) or ribonucleic acid (RNA, including messenger RNA or mRNA), genomic or recombinant, biologically isolated or synthetic.

The DNA molecule can be a cDNA molecule, which is a DNA copy of a messenger RNA (mRNA) encoding the F11 receptor.

An example of a nucleic acid molecule which encodes a human platelet F11 receptor is the molecule having the nucleotide sequence as shown in SEQ ID NO:1. Nucleotides 16–96 of SEQ ID NO:1 represent a signal sequence, and nucleotides 97–912 represent the mature protein (nucleotides 16–912 thus represent the F11 receptor with its signal sequence). Nucleotides 16–18 are an ATG start codon, and nucleotides 913–915 are a stop codon. The amino acid sequence encoded by this nucleotide sequence is shown in SEQ ID NO:3. Amino acid residues 1–27 of SEQ ID NO:3 represent the signal sequence, and amino acid residues 28–299 represent the mature protein (amino acid residues 1–299 thus represent the F11 receptor with its signal sequence). This F11 receptor is designated F11R-A. Another example of a nucleic acid molecule which encodes a human platelet F11 receptor is the molecule having the nucleotide sequence as shown in SEQ ID NO:2. Nucleotides 16–96 of SEQ ID NO:2 represent a signal sequence, and nucleotides 97–594 represent the mature protein (nucleotides 16–594 thus represent the F11 receptor with its signal sequence). Nucleotides 16–18 are an ATG start codon, and nucleotides 595–597 are a stop codon. The amino acid sequence encoded by this nucleotide sequence is shown in SEQ ID NO:4. Amino acid residues 1–27 of SEQ ID NO:4 represent the signal sequence, and amino acid residues 28–193 represent the mature protein (amino acid residues 1–193 thus represent the F11 receptor with its signal sequence). This F11 receptor is designated F11R-B.

The invention also provides an antisense nucleic acid molecule that is complementary to at least a portion of the mRNA encoding the human platelet F11 receptor. Antisense nucleic acid molecules can be RNA or single-stranded DNA, and can be complementary to the entire mRNA molecule encoding the F11 receptor (i.e. of the same nucleotide length as the entire molecule). It may be desirable, however, to work with a shorter molecule. In this instance, the antisense molecule can be complementary to a portion of the entire mRNA molecule encoding the F11 receptor. These shorter antisense molecules are capable of hybridizing to the mRNA encoding the entire molecule, and preferably consist of about twenty to about one hundred nucleotides. These antisense molecules can be used to reduce levels of human platelet F11 receptor, by introducing into cells an RNA or single-stranded DNA molecule that is complementary to at least a portion of the mRNA of the F11 receptor (i.e. by introducing an antisense molecule). The antisense molecule can base-pair with the mRNA of the F11 receptor, preventing translation of the mRNA into protein. Thus, an antisense molecule to the F11 receptor can prevent translation of mRNA encoding the F11 receptor into a functional F11 receptor protein.

More particularly, an antisense molecule complementary to at least a portion of mRNA encoding a human platelet F11 receptor can be used to decrease expression of a functional F11 receptor. A cell with a first level of expression of a functional human platelet F11 receptor is selected, and then the antisense molecule is introduced into the cell. The antisense molecule blocks expression of functional human platelet F11 receptor, resulting in a second level of expression of a functional human platelet F11 receptor in the cell. The second level is less than the initial first level.

Antisense molecules can be introduced into cells by any suitable means. In one embodiment, the antisense RNA molecule is injected directly into the cellular cytoplasm, where the RNA interferes with translation. A vector may also be used for introduction of the antisense molecule into a cell. Such vectors include various plasmid and viral vectors. For a general discussion of antisense molecules and their use, see Han et al. 1991 and Rossi 1995.

The invention further provides a special category of antisense RNA molecules, known as ribozymes, having recognition sequences complementary to specific regions of the mRNA encoding the human platelet F11 receptor. Ribozymes not only complex with target sequences via complementary antisense sequences but also catalyze the hydrolysis, or cleavage, of the template mRNA molecule. Examples, which are not intended to be limiting, of suitable regions of the mRNA template to be targeted by ribozymes are any of the homologous regions identified by comparing the various F11 receptors.

Expression of a ribozyme in a cell can inhibit gene expression (such as the expression of a human platelet F11 receptor). More particularly, a ribozyme having a recognition sequence complementary to a region of a mRNA encoding a human platelet F11 receptor can be used to decrease expression of human platelet F11 receptor. A cell with a first level of expression of human platelet F11 receptor is selected, and then the ribozyme is introduced into the cell. The ribozyme in the cell decreases expression of human platelet F11 receptor in the cell, because mRNA encoding the human platelet F11 receptor is cleaved and cannot be translated.

Ribozymes can be introduced into cells by any suitable means. In one embodiment, the ribozyme is injected directly into the cellular cytoplasm, where the ribozyme cleaves the mRNA and thereby interferes with translation. A vector may be used for introduction of the ribozyme into a cell. Such vectors include various plasmid and viral vectors (note that the DNA encoding the ribozyme does not need to be "incorporated" into the genome of the host cell; it could be expressed in a host cell infected by a viral vector, with the vector expressing the ribozyme, for instance). For a general discussion of ribozymes and their use, see Sarver et al. 1990, Chrisey et al. 1991, Rossi et al. 1992, and Christoffersen et al. 1995.

The nucleic acid molecules of the subject invention can be expressed in suitable host cells using conventional techniques. Any suitable host and/or vector system can be used to express the human platelet F11 receptor. For in vitro expression, bacterial hosts (for example, *Escherichia coli*) and mammalian hosts (for example, Hela cells, Cv-1 cells, COS cells) are preferred. For in vivo expression, the most suitable host cell depends on the goal of the expression.

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into suitable host cells. For example, DNA encoding the human platelet F11 receptor can be injected into the nucleus of a host cell or transformed into the host cell using a suitable vector, or mRNA encoding the human platelet F11 receptor can be injected directly into the host cell, in order to obtain expression of the human platelet F11 receptor in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures. DNA can also be incorporated into artificial lipid vesicles, liposomes, which fuse with the cell membrane, delivering their contents directly into the cytoplasm. In an even more direct approach, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. One such virus widely used for protein production is an insect virus, baculovirus. For a review of baculovirus vectors, see Miller (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

Host cells into which the nucleic acid encoding the human platelet F11 receptor has been introduced can be used to produce (i.e. to functionally express) the human platelet F11 receptor. The function of the encoded human platelet F11 receptor can be assayed according to methods known in the art.

Having identified the nucleic acid molecules encoding human platelet F11 receptors and methods for expressing the human platelet F11 receptors encoded thereby, the invention further provides a method of screening a substance (for example, a compound or inhibitor) for the ability of the substance to modify F11 receptor function. The method comprises introducing a nucleic acid molecule encoding the human platelet F11 receptor into a host cell, and expressing the human platelet F11 receptor encoded by the molecule in the host cell. The cell is then exposed to a substance and evaluated to determine if the substance modifies the function of the F11 receptor. From this evaluation, substances effective in altering the function of the F11 receptor can be found. Such agents may be, for example, small molecule inhibitors, chemicals, peptides, antibodies, etc.

The evaluation of the cell to determine if the substance modifies the function of the F11 receptor can be by any means known in the art.

The nucleic acid molecules of the subject invention can be used either as probes or for the design of primers to obtain DNA encoding other human platelet F11 receptors by either cloning and colony/plaque hybridization or amplification using the polymerase chain reaction (PCR).

Specific probes derived from SEQ ID NO:1 or SEQ ID NO:2 (or portions thereof) can be employed to identify colonies or plaques containing cloned DNA encoding a member of the human platelet F11 receptor family using known methods (see Sambrook et al. 1989). One skilled in the art will recognize that by employing such probes under high stringency conditions (for example, hybridization at 42° C. with 5×SSPC and 50% formamide, washing at 50–65° C. with 0.5×SSPC), sequences having regions which are greater than 90% homologous or identical to the probe can be obtained. Sequences with lower percent homology or identity to the probe, which also encode human platelet F11 receptors, can be obtained by lowering the stringency of hybridization and washing (e.g., by reducing the hybridization and wash temperatures or reducing the amount of formamide employed)

More particularly, in one embodiment, the method comprises selection of a DNA molecule encoding a human platelet F11 receptor, or a fragment thereof, the DNA molecule having a nucleotide sequence as shown in SEQ ID NO:1, nucleotides 16–912 of SEQ ID NO:1, nucleotides 97–912 of SEQ ID NO:1, SEQ ID NO:2, nucleotides 16–594 of SEQ ID NO:2, or nucleotides 97–594 of SEQ ID NO:2, and designing an oligonucleotide probe for human platelet F11 receptor based on the nucleotide sequence of the selected DNA molecule. A genomic or cDNA library of an organism is then probed with the oligonucleotide probe, and clones are obtained from the library that are recognized by the oligonucleotide probe so as to obtain DNA encoding another human platelet F11 receptor.

Specific primers derived from SEQ ID NO:1 or SEQ ID NO:2 (or portions thereof) can be used in PCR to amplify a DNA sequence encoding a member of the human platelet F11 receptor family using known methods (see Innis et al. 1990). One skilled in the art will recognize that by employing such primers under high stringency conditions (for example, annealing at 50–60° C., depending on the length and specific nucleotide content of the primers employed), sequences having regions greater than 75% homologous or identical to the primers will be amplified.

More particularly, in a further embodiment the method comprises selection of a DNA molecule encoding human platelet F11 receptor, or a fragment thereof, the DNA molecule having a nucleotide sequence as shown in SEQ ID NO:1, nucleotides 16–912 of SEQ ID NO:1, nucleotides 97–912 of SEQ ID NO:1, SEQ ID NO:2, nucleotides 16–594 of SEQ ID NO:2, or nucleotides 97–594 of SEQ ID NO:2, designing degenerate oligonucleotide primers based on the nucleotide sequence of the selected DNA molecule, and employing such primers in the polymerase chain reaction using as a template a DNA sample to be screened for the presence of human platelet F11 receptor-encoding sequences. The resulting PCR products can be isolated and sequenced to identify DNA fragments that encode polypeptide sequences corresponding to the targeted region of human platelet F11 receptor.

Various modifications of the nucleic acid and amino acid sequences disclosed herein are covered by the subject invention. These varied sequences still encode a functional human platelet F11 receptor. The invention thus further provides an isolated nucleic acid molecule encoding a human platelet F11 receptor, the nucleic acid molecule encoding a first amino acid sequence having at least 90% amino acid identity to a second amino acid sequence, the second amino acid sequence having an amino acid sequence selected from the group consisting of SEQ ID NO:3, amino acid residues 28–299 of SEQ ID NO:3, SEQ ID NO:4, and amino acid residues 28–193 of SEQ ID NO:4. In further embodiments, the first amino acid sequence has at least 95%, 96%, 97%, 98%, or 99% amino acid identity to SEQ ID NO:3, amino acid residues 28–299 of SEQ ID NO:3, SEQ ID NO:4, or amino acid residues 28–193 of SEQ ID NO:4.

The invention further provides an isolated DNA oligomer capable of hybridizing to the nucleic acid molecule encoding the human platelet F11 receptor according to the subject invention. Such oligomers can be used as probes in a method of detecting the presence of human platelet F11 receptor in a sample. More particularly, a sample can be contacted with the DNA oligomer and the DNA oligomer will hybridize to any human platelet F11 receptor present in the sample, forming a complex therewith. The complex can then be detected, thereby detecting presence of human platelet F11 receptor in the sample.

The complex can be detected using methods known in the art. Preferably, the DNA oligomer is labeled with a detectable marker so that detection of the marker after the DNA oligomer hybridizes to any human platelet F11 receptor in the sample (wherein non-hybridized DNA oligomer has been washed away) is detection of the complex. Detection of the complex indicates the presence of human platelet F11 receptor in the sample. As will be readily apparent to those skilled in the art, such a method could also be used quantitatively to assess the amount of human platelet F11 receptor in a sample.

For detection, the oligomers can be labeled with, for example, a radioactive isotope, biotin, an element opaque to X-rays, or a paramagnetic ion. Radioactive isotopes are commonly used and are well known to those skilled in the art. Representative examples include indium-111, technetium-99m, and iodine-123. Biotin is a standard label which would allow detection of the biotin labeled oligomer with avidin. Paramagnetic ions are also commonly used and include, for example, chelated metal ions of chromium (III), manganese (II), and iron (III). When using such labels, the labeled DNA oligomer can be imaged using methods known to those skilled in the art. Such imaging methods include, but are not limited to, X-ray, CAT scan, PET scan, NMRI, and fluoroscopy. Other suitable labels include enzymatic labels (horseradish peroxidase, alkaline phosphatase, etc.) and fluorescent labels (such as FITC or rhodamine, etc.).

Fragments of the nucleic acid molecules encoding the F11 receptor are also provided, and are best defined in the context of amino acid sequence relationships among members of the F11 receptor sequence family and information on the function of specific F11 receptor domains.

The F11 receptor molecule of the subject invention can include a leader or signal sequence (for example, for targeting of the F11 receptor to the desired part of a cell). The leader can include an ATG start codon encoding a methionine residue. In fact, SEQ ID NOs:1–4 each include a signal sequence (amino acid residues 1–27 of SEQ ID NOs:3 and 4, encoded by nucleotides 16–96 of SEQ ID NOs:1 and 2, respectively). All versions of the Fl receptor (with and without 3' and 5' non-coding regions, and with and without the signal sequence) are thus specifically intended to be covered herein.

In some methods of the invention, tissues or cells are contacted with or exposed to a substance, including, for example, a composition or a compound. In the context of this invention, to "contact" tissues or cells with or to "expose" tissues or cells to a substance means to add the substance, usually in a liquid carrier, to a cell suspension or tissue sample, either in vitro or ex vivo, or to administer the substance to cells or tissues within an animal (including humans).

Having thus detailed the various aspects of the subject invention, the stimulatory anti-human platelet monoclonal antibody, termed M.Ab.F11 (IgG1 isotype) was identified and characterized previously as an agonist which induces platelet aggregation and granule secretion (Kornecki et al. 1990). The biochemical pathway by which M.Ab.F11 induces platelet aggregation and secretion was shown to involve recognition by M.Ab.F11 of a platelet surface protein duplex termed the F11 receptor (Kornecki et al. 1990) (also called FAM, the F-11 Adhesion Molecule). This initial recognition of FAM was followed, in part, by crosslinking of the antibody through the Fc domain to the platelet FcγRII receptor (Naik et al. 1995). The binding of M.Ab.F11 to intact platelets resulted in the activation of signal transduction pathways leading to a transient, reversible translocation of PKC isozymes α and ζ from the cytoplasm to the membrane as well as a sustained, irreversible association of PKC isoenzymes δ, β, η' and θ at the plasma membrane (Wang et al. 1995). In addition, activation of platelets with M.Ab.F11 resulted in increased intracellular phosphorylation of p47, the protein kinase C substrate pleckstrin, and p20, the light chain fragment of myosin, which is also a substrate for myosin light chain kinase (Kornecki et al. 1990; Kornecki et al. 1995). The involvement of the fibrinogen receptor, the GPIIb/IIIa complex, in M.Ab.F11-induced platelet activation was shown by use of an anti-GPIIIa antibody which completely blocked the antibody-induced platelet aggregation and secretion (Kornecki et al. 1990).

FAM was initially identified immunologically as two membrane proteins of molecular weight of 32 and 35 kDa (Kornecki et al. 1990). Following the purification of FAM by ion exchange and affinity chromatography, N-deglycosylation of either the 32 or 35 kDa protein resulted in the formation of a deglycosylated core protein of 29 kDa, recognized by M.Ab.F11 (Naik et al. 1995). Subsequently, twenty-six amino acids of the N-terminus of this protein were published (Naik et al. 1995) (SEQ ID NO:14: SVTVHSSEPEVRIPENNPVKLSXAYS)(NCB Accession # S56749), and several internal amino acid sequences, including forty-three amino acids of the endoproteinase (V8 protease) Glu-C proteolytic fragment (SEQ ID NO:15:WKFDQGDTTRLVEYNNKITASYEDRVTFLPT-GITFKSVTRED) were detailed (Naik et al. 1995). Extensive data base searches performed at that time indicated that this molecule represented a new receptor on the platelet surface.

In accordance with the present invention, the internal forty-three amino acid sequence of this molecule was utilized for the isolation of a cDNA encoding the full length FAM molecule. Sequence analysis demonstrated that FAM is an integral membrane protein and a novel member of the immunoglobulin superfamily. It was shown to be present in platelets, endothelial cells and other cells of the hematopoietic system. Furthermore, autoantibodies developed against FAM were detected in the circulation of thrombocytopenic and renal disorder patients indicating that such antibodies may contribute to the activation of platelets in vivo.

Experimental Methods

Reagents. Electrophoresis-pure reagents, including acrylamide, ammonium persulfate, nitrocellulose, SDS, and TEMED were purchased from BioRad (Hercules, Calif.). The 5'and 3' RACE systems were purchased from GIBCO BRL, the AdvanTAge PCR Cloning Kit from Clontech, the QIAprep Miniprep kit and the Rneasy Mini kit from Qiagen (Valencia, Calif.), Tag DNA polymerase and restriction endonuclease Eco RI were purchased from Boehringer Mannheim (Indianapolis, Ind.). Fetal bovine serum was obtained from HyClone (Logan, Utah). All other reagents were obtained from Sigma (St. Louis, Mo.) and were of the highest reagent grade.

Platelet isolation. Venous blood, obtained from healthy volunteers, was collected into the anticoagulatent ACD (pH4.6) as previously described (Kornecki et al. 1990). The platelet-rich plasma (PRP) fraction was obtained by centrifugation (160×g, 10 min.) and platelets were isolated in the presence of platelet aggregation inhibitors are described previously (Kornecki et al. 1990; Naik et al. 1995).

RNA isolation and processing. RNA was isolated in the following manner: isolated platelets were solubilized in "lysis buffer" (4M guanidine isothiocyanate, 25 mM sodium citrate, 0.5% sodium sarcosine and 100 mM β-mercaptoethanol) dissolved in DEPC-treated water (Chomczynski and Sacchi 1987), passed 10–15× through a 21-gauge needle, diluted ten-fold with 2M sodium acetate (pH 4.0), and the RNA extracted by vigorous vortexing in the presence of an equal amount of the mixture containing volumes of phenol (pH 4.0) and 1 volume of chloroform-isoamyl alcohol (29:1). The crude platelet RNA was precipitated with an equal volume of isopropanol. The precipitate was resolubilized in the "lysis buffer" and reprecipitated as above. For long-term storage, the RNA was kept as an isopropanol precipitate at −80° C. Immediately before RT-PCR amplification, the RNA was quantitated and its purity tested by measuring its absorbance at 260/280 nm. The quality of the isolated RNA was also tested by agarose gel electrophoresis.

Reverse Transcriptase-Polymerase Chain Reaction (RT-PCR) with degenerate primers. Reverse transcriptase reactions were carried-out using 1 μg of the total RNA and the oligo d(T)16 primers using the Perkin Elmer kit as detailed in the manufacturer's protocol. The Polymerase Chain Reaction (PCR) was carried-out using degenerate primer pairs derived from the partial amino acid sequence of the F11 receptor termed Glu-C (fragment 4), as previously described (Naik et al. 1995). The final concentration of each primer was 2 pmol/μl, while dNTP's and $Mg^{2+}$ were present at 200 μM and 2 mM, respectively. The PCR mix not containing the Taq polymerase was subjected to hot start at 99° C. for 10 minutes followed by addition of the polymerase at 85° C. to the final concentration of 1.25U per 50 μl reaction. Thermocycling consisted of 5 cycles at 95° C. for 1 min, 48° C. for 2 min and 72° C. for 2 min, followed by 45 cycles at 94° C. for 1 min, 48° C. for 2 min and 72° C. for 2 min with a 1 sec extension per each subsequent cycle to compensate for the losses in Taq polymerase activity. The final extension was performed at 72° C. for 5 min. Upon completion of PCR, samples were kept frozen and subjected to PAGE within several hours.

The names and sequences of the degenerate primers derived from the partial protein sequence of the F11 receptor were as follows: F11/f-6 (SEQ ID NO:16: GARTAYAAYAAYAARATHAC), F11/r-5(A) (SEQ ID NO:17: TTRAANGTDATNCCNGTAGG), F11/r-5(C) (SEQ ID NO:18: TTRAANGTDATNCCNGTCGG), F11/r-5(G) (SEQ ID NO:19: TTRAANGTDATNCCNGTGGG), F11/r-5(T) (SEQ ID NO:20: TTRAANGTDATNCCNGTTGG). Primers used for 3' and 5'-RACE procedures were as follows: GSP1(SEQ ID NO:21: AGCTTCCTATGAGGACCGGG), GSP2 (SEQ ID NO:22: GTCACGGACTTGAAGGT), GSP4 (SEQ ID NO:23: GGCAAGAAGGTCACCCGGTCC), GSP3 (SEQ ID NO:24: TTRAANGTDATNCCNGTTGG), Adapter Abridged Universal Amplification Primers (AP and AUAP, GIBCO), 3'-F11-6F (SEQ ID NO:25: ATCTGGTTTGCCTATAGCCG), 3'-F11-6R (SEQ ID NO:26: CTCTAGCCTCTAATTCCCGC).

DNA analysis by polyacrylamide gel electrophoresis (PAGE). The DNA samples (PCR products or plasmid DNA) were separated by electrophoresis in 15% polyacrylamide slab minigels. Molecular weight standards of 50 bp DNA Ladder™, 100 bp DNA Ladder™ or 123 bp DNA Ladder™ (Gibco BRL, Gaithersburg, Md.) were used to estimate the approximate molecular weight of each DNA band. The gels were stained with ethidium bromide (5 μg/ml), destained in distilled water and visualized using UV. Long wavelength UV (366nm) was used when the resolved DNA fragments were subsequently subjected to purification and cloning.

Purification and cloning of the amplified PCR products. Following PAGE, the DNA fragment was eluted by the standard "Crush and Soak Method" as described (Sambrook et al. 1989). The eluted DNA was digested with 1U of T4 DNA polymerase in the presence of 100 μM DNTP, to remove the protruding 3'-A overhangs, and the resulting blunt-ended product was phosphorylated at its 5' ends. The cloning vector, pBLUESCRIPT SK+(Stratagene, La Jolla, Calif.) was linearized with SmaI and its 5'-ends dephosphorylated by two treatments with calf intestinal alkaline phosphatase. Blunt end ligation was performed at 15° C. for 18 hrs in the presence of T4 ligase. The molar ratio of insert to vector was approximately 5:1. The subsequent construct was transformed into DH5a competent cells (Gibco BRL, Gaithersburg, Md.) as suggested by the manufacturer. The plasmid DNA was isolated using the Wizard™ Midipreps DNA purification system (Promega, Madison, Wis.). The presence of the cloned insert was confirmed by KpnI and SacI digestion of the purified plasmid DNA. Nineteen colonies were selected as positive and five of them have been sequenced.

DNA Sequencing. The isolated and purified plasmid DNA was sequenced by ACGT (Northbrook, Ill.). The fidelity of the data was confirmed by sequencing both strands using M13 universal forward and reverse primers.

3' Rapid AmDlification of CDNA Ends (3'RACE). This procedure was used for the amplification of nucleic acid sequences from a mRNA template between the internal site of the Glu-C (fragment 4) determined above (SEQ ID NO:21: 5' AGCTTCCTATGAGGACCGGG 3', GSP1) and the 3' end of the mRNA. Total platelet RNA (0.5 μg) was prepared as described above. RT was carried-out using reverse transcriptase and the AP primer as described in the 3' RACE system (Gibco/BRL). The original mRNA template was destroyed with RNAse H. PCR was carried-out using the sequence-specific primer GSP1 and the Abridged Universal Amplification Primer (AUAP). Thirty-five cycles at 94° C. for 5 sec, 58° C. for 15 sec, and at 72° C. for 3 min were performed. The final extension was performed at 72° C. for 3 min. The PCR product was cloned into pT-Adv vector (Clontech, Palo Alto, Calif.) as described by the manufacturer. The plasmid DNA was subsequently purified using a QIAprep Miniprep Kit (QIAGEN, Valencia, Calif.) following procedures described in the QIAprep miniprep handbook. Purified plasmid DNA was digested with EcoRI (Boehringer Manheim) following the manufacturer's protocol. The presence of the PCR product was confirmed using agarose gel electrophoresis (Sambrook et al. 1989). Six independent clones were sequenced by ACGT (Northbrook, Ill.). One clone was sequenced in the forward and reverse direction using M13R and T7 universal primers. Four clones were sequenced on one strand, and one clone was sequenced on both directions using M13R, M13F and the sequence specific primers: GSP1, 3'-F11-6 forward primer (SEQ ID NO:25), and 3'-F11-6 reverse primer (SEQ ID NO:26). The GSP1 custom primer was synthesized by Ransom Hill Bioscience, and the 3'-F11-6 forward and 3'-F11-6 reverse primers were synthesized by Gibco/BRL.

5' Rapid Amplification of cDNA Ends (5'-RACE). Total RNA was isolated from freshly-prepared human platelets (from 100 ml of whole blood) using a RNeasy Mini Kit (QIAGEN, Valencia, Calif.) following the procedures described in the manufacturer's RNeasy Mini Handbook. The 5'-RACE system for Rapid Amplification of cDNA Ends (Version 2.0) (Gibco/BRL) was used to amplify the 5' end of the F11 cDNA following procedures detailed in the manufacturer's manual. The first strand cDNA synthesis was primed using the gene-specific, antisense oligonucleotide (GSP2, SEQ ID NO:22: GTCACGGACTTGAAGGT). The product was purified from unincorporated dNTPs and GSP2 using a GlassMax DNA Isolation Spin Cartridge included in the kit. A homopolymeric tail was subsequently added to the 3'-end of the cDNA using terminal deoxynucleotidyl transferase and dCTP. The dC-tailed cDNA was amplified by PCR using the gene-specific primer 3 (GCP3) (F11/r-5(RT), SEQ ID NO:27: TTRAANGTDATNCCRGTTGG and the Abridged Universal Anchor Primer (AUAP). Forty-five cycles at 94° C. for 30 sec, 48° C. for 1 min, and at 72° C. for 3 min were performed, followed by a final extension at 72° C. for 3 min. The diluted (1/100) primary PCR products were reamplified using a nested, gene specific primer 4 (GSP4, SEQ ID NO:23: GGCAAGAAGG-TCACCCGGTCC) and Abridged Universal Amplification Primer (AUAP). Thirty-five cycles at 94° C. for 30 sec, 55° C. for 1 min, and at 72° C. for 3 min were performed, followed by a final extension at 72° C. for 3 min. The resulting PCR products were cloned into pT-Adv vector (Clontech, Palo Alto, Calif.) and analyzed as described above for the 3' RACE system. Three clones were sequenced by ACGT (Northbrook, Ill.), two clones in both directions using M13R and M13F universal primers, and one clone on one strand. All custom primers used for 5'-RACE procedure were synthesized by Gibco/BRL.

Data analysis. The translated amino acid sequence of FAM was analyzed using the following software programs: TMpred, FASTA, ScanProsite, PfamHMM, PSORT, SSPRED, ProfileScan, ProtScale, PatScan, pI/Mw and Motif, SignalP, Pfam (The Sanger Centre) and Simple Modular Architecture Research Tool.

Cell preparation and cell culture. HEL cells were purchased from the American Type Culture Collection. Megakaryocytic cell lines (CMK, CMK11-5 and CMK6) were obtained through the generous gift of Dr. H. Avraham, Hematology and Oncology Research Laboratory, New England Deacones Hospital of Boston, Mass. Cells were maintained in RPMI 1640 medium supplemented with 10% FBS. Bovine aortic endothelial cells (BAEC) were obtained from Dr. George Tuszynski of the Medical School of Pennsylvania, Pa. The human endothelial hybrid cell line (Eahy926) was obtained from Dr. Cora-Jean S. Edgell, University of North Carolina, Chapel Hill, N.C. The Eahy926 cells were cultured in Dulbecco's modified Eagle's medium containing 10% heat inactivated FBS and HAT (100 $\mu$mol hypoxanthine, 0.4 $\mu$mol aminopterin, and 16 $\mu$mol thymidine) in a humidified atmosphere containing 5%$CO_2$. The K562 cell line was maintained in a 15% FBS-RPMI medium.

Electrophoresis and immunoblotting. Samples were prepared for SDS-PAGE as follows: for the preparation of RBC ghosts, the procedure of Schwoch and Passow was used (Schwoch and Passow 1973). Cell extracts of HEL, K562, CMK, CMK6 and CMK11-5 cells were prepared as follows: cells were harvested, washed with PBS, and solubilized in Laemmli buffer. Eahy926, HUVEC, and BAEC cells were treated with 10 mM EDTA-PBS, harvested, washed, suspended in Laemmli buffer and processed for SDS-PAGE (Bio-Rad). Proteins were transferred onto nitrocellulose membranes and incubated for 16 hrs with the primary monoclonal (M.Ab.F11) or rabbit polyclonal FAM antibodies (4 $\mu$g/ml) or purified human antibodies, followed by incubation for 2 hrs with secondary antibodies, rabbit or goat anti-mouse/human Ig-AP conjugates (1:4000).

Flow cytometry. The CMK, CMK11-5, CMK6, HEL and K562 cell lines were washed with PBS and resuspended in 0.1% BSA/PBS buffer. HUVEC, Eahy926 and bovine endothelial cells were treated with 10 mM EDTA/PBS, washed with PBS and finally with 0.1% BSA/PBS. To isolate the buffy coat fraction, whole blood was mixed with equal amount of HBS buffer, overlaid on Ficoll and centrifuged. The buffy coat layer and erythrocytes were collected separately. For flow cytometry analysis, the cells were resuspended in 0.1% BSA/PBS at the final concentration of $4 \times 10^5$ cells/sample and incubated with M.Ab.F11 (5 $\mu$g/ml) or with an isotype identical nonreactive IgG (used as a control). Following a 1 hr incubation at 22° C., the cells were washed with 0.1% BSA/PBS buffer, treated with 50 $\mu$l of 1/100 diluted goat anti-mouse Ig-FITC (GAM), incubated for 30 min on ice, washed with 0.1% BSA/PBS and resuspended in 0.1% BSA/PBS. The samples were analyzed using a Becton Dickinson Immunocytometry Systems flow cytometer (Becton Dickinson FAC Sort, San Jose, Calif.). Flow cytometric analysis of human platelets was performed in the presence of $PGE_1$.

Preparation of antibodies. M.Ab.F11 was identified and characterized as previously described (Kornecki et al. 1990). A polyclonal antibody directed to the twenty-one amino acid N-terminal sequence of the F11 receptor (SEQ ID NO:5: SVTVHSSEPEVRIPENNPVKLS, detailed in Naik et al. 1995) was prepared in rabbits by Qualify Controlled Biochemicals, Inc (Hopkinton, Mass.) and subsequently purified by affinity chromatography.

Screening for FAM antibodies in patients. The presence of anti-FAM antibodies in the circulation of several patients was examined. Serum was obtained from a 64 year old male with a history of hypertension following two separate cerebrovascular accidents within a two-week period. While workup revealed no obvious source of the infarcts (carotid dopplers were normal and no thrombus was detected), the patient developed an aspiration pneumonia and was treated with antibiotics. He developed acute renal failure and dialysis was initiated. At this time, his platelet count decreased from an admission level of 266,000/ml to 50,000/ml. The patient developed bilateral gangrene of both legs. Although the patient had received heparin, it was only after the gangrene had developed, thus excluding a diagnosis of heparin-induced thrombocytopenia. The patient died three weeks after hospitalization due to overwhelming sepsis, respiratory failure and cardiac failure. Another patient examined for the presence of FAM antibodies in his circulation was a 40 year old male who had end-stage renal disease secondary to hypertension. He had a cadaveric kidney transplant and was receiving the immune suppressive drug, tacrilimus (FK506).

EXAMPLE I

Immunological Detection of FAM in Platelet Membranes.

It has been previously shown that monoclonal antibody F11 is able to detect two platelet membrane glycoproteins of 32 and 35 kDa, which have now been designated as FAM (Kornecki et al. 1990; Naik et al. 1995). For verification of the presence of FAM molecules as constituents of the platelet membrane, a polyclonal antibody was developed against the N-terminal portion of FAM, the twenty-one amino acid sequence which has previously been reported (Naik et al. 1995), and immunoblotting was used for the detection of these proteins. As shown in FIG. 1, immunoblotting of platelet proteins with the N-terminal, anti-FAM polyclonal antibody revealed the presence of both the 32/35 kDa glycoproteins in the platelet membrane. These results were found to be identical to those obtained previously when the monoclonal antibody F11 was used for the detection of this duplex (Kornecki et al. 1990; Naik et al. 1995).

EXAMPLE II

Cloning of the F11R cDNA.

The amino acid sequence of the N-terminal portion of FAM molecule receptor and that of several peptides obtained following proteolytic digestion of the purified receptor were published previously (Naik et al. 1995). Based on the amino acid sequence of one of the fragments, Glu-C(fragment 4), containing SEQ ID NO:15:WKFDQGDTTRLVEYNNKITASYEDRVTFLPT-GITFKSVTRED, four degenerate oligonucleotide primers (differing only by a single base, F 11/r-5(A), F11/r-5(C), F11/r-5(G), F11/r-5(T) and the forward primer F11/f-6 were designed and synthesized as described in the Experimental Methods section. Using platelet RNA and the designed primers, RT-PCR of the C-terminal portion of Glu-C (fragment 4) was carried-out. The PCR-amplified product was sequenced and translated. It was determined that the translated amino acid sequence of the internal section of this product was identical to the internal amino acid sequence of the published Glu-C(fragment4) detailed above.

In order to obtain the full FAM cDNA sequence, procedures were used which employed both the 5' and the 3' RACE techniques. The 3' RACE procedure used a 5' primer based on the nondegenerate sequence which was determined by PCR based on the reverse translation of the middle portion of Glu-C(fragment 4). The sequence of the 5' end of the 3' RACE clones was consistent with the predicted (degenerate) sequence obtained by reverse translation of the C-terminal and of the Glu-C (fragment 4) peptide.

5' RACE was carried-out using nested primers, the sequences of which were directly derived from the 5' end of the clone obtained by the 3' RACE procedure. Analysis of the 5' RACE products revealed a reading frame containing the previously determined N-terminus of FAM (Naik et al. 1995), and the 26 N-terminal amino acids of the Glu-C (fragment 4) peptide (Naik et al. 1995). The protein N-terminus was preceded by a signal sequence with a translation initiation codon having a consensus flanking sequence PuXXAUGG (Kozak 1987a; Kozak 1987b). The complete FAM cDNA and the deduced amino acid sequence are shown in FIG. 2.

EXAMPLE III

Analysis of the FAM Amino Acid Sequence.

Features of FAM apparent from analysis of the amino acid sequence are summarized in Table 1. FAM expressed on human platelets is encoded by an mRNA of 1821 bases which upon translation yield a protein of 299 amino acids with a molecular weight of 29,682 kDa. The estimated value of the isoelectric point was 6.72 (Bjellqvist et al. 1993; Bjellqvist et al. 1994). The mature protein (minus the signal sequence) has an amino acid sequence of 272 amino acids (amino acid residues 28–299 of SEQ ID NO:3).

Figure 3:
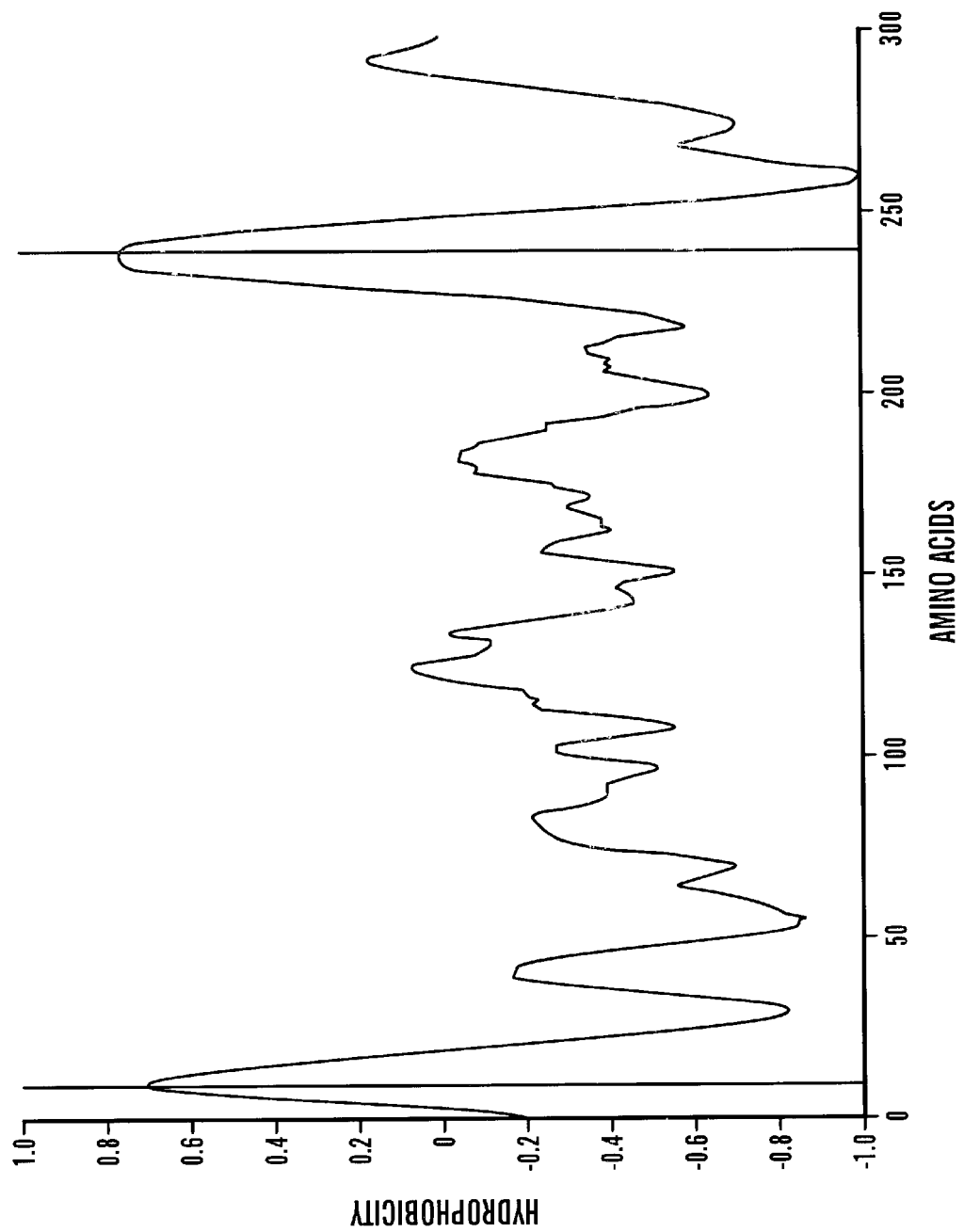
FIG. 3 is a hydrophobicity plot of amino acid sequences of FAM. The transmembrane domain was found in the region spanning amino acids 239 to 258 of SEQ ID NO:3, and the signal peptide sequence is found at amino acids 12 to 29 of SEQ ID NO:3.

Further data-base searches of potential membrane localization and orientation sites suggested that FAM is an integral membrane protein with a potential transmembrane domain (amino acids 239 to 258 of SEQ ID NO:3), a cytoplasmic-oriented C-terminus (amino acids 255 to 299 of SEQ ID NO:3), and an extracellular N-terminus (amino acids 28 to 239 of SEQ ID NO:3), and contains a cleavable signal sequence corresponding to amino acids 1 to 27 of SEQ ID NO:3 (Nielsen et al. 1997; Singer 1990). Also, these analyses indicated that FAM contains one potential N-glycosylation site (Bause 1983; Gavel and von Heijne 1990; Miletich and Broze 1990). The cytoplasmic tail of the FAM was shown to contain two phosphorylable tyrosine residues at positions 260 and 279 of SEQ ID NO:3 as well as putative intracellular and extracellular sites of phosphorylation by casein kinase II (Pinna 1990), protein kinase C (Woodget et al. 1986; Kishimoto et al. 1985) and cAMP- or cGMP-dependent protein kinases (Glass and Smith 1983; Glass et al. 1986). Hydrophobicity analysis of the FAM amino acid sequence, performed using the ProtScale program following the method of Kyte and Doolittle (Kyte and Doolittle 1982), is shown in FIG. 3.

EXAMPLE IV

FAM is a Novel Ig Superfamily Member

Figure 5:
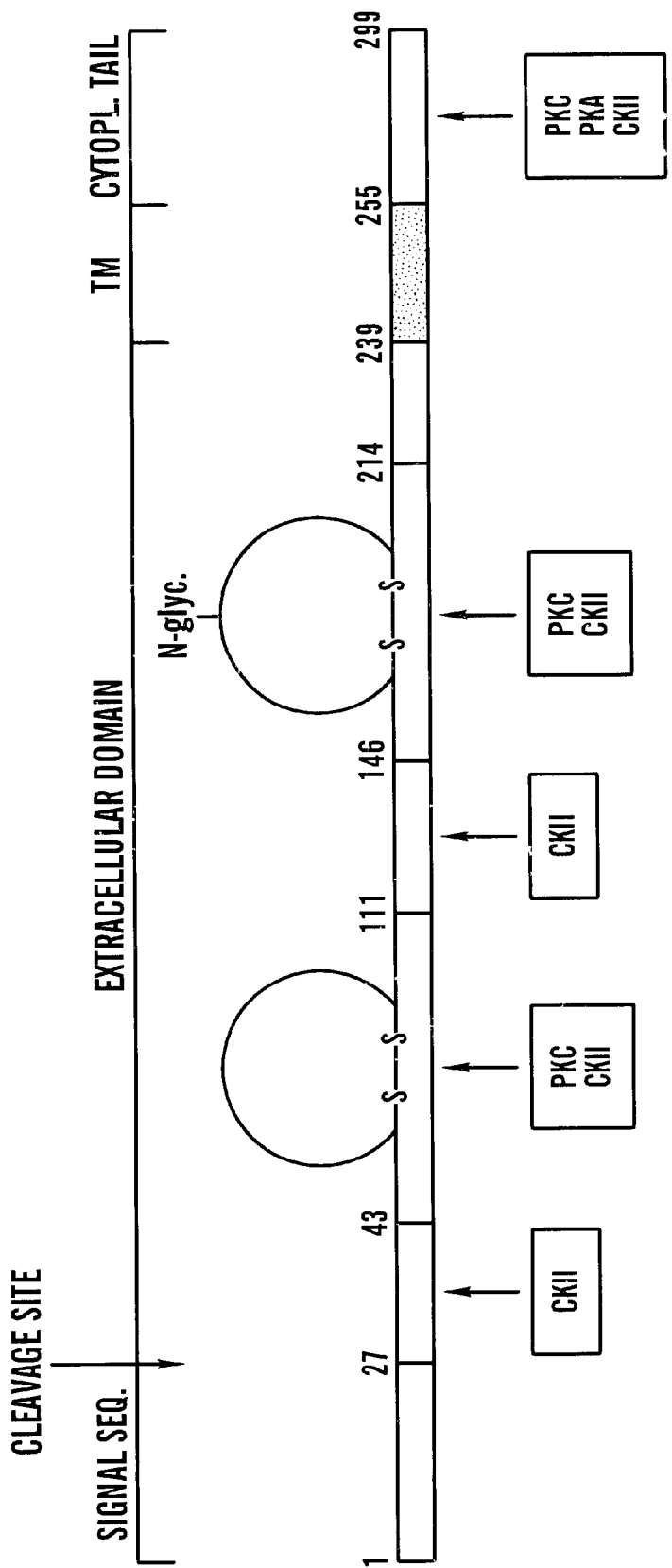
FIG. 5 is a figure of a schematic model illustrating the main deduced structural features of FAM. TM indicates the transmembrane region of FAM (shaded region)

A combined literature and protein database search of sequences homologous to FAM revealed that FAM exhibits two regions (amino acids 41 to 116 and 144 to 219 of SEQ ID NO:3; SEQ ID NOs:9 and 11, respectively) of high homology to members of the immunoglobulin superfamily (IGSF) (Kyte and Doolittle 1982; Williams and Barclay 1988; Williams et al. 1989; Bork et al. 1994; Brummendorf and Rathjen 1995; Karplus et al. 1997; Schultz et al. 1998). These two amino acid sequences, representing putative Ig domains, were compared to the conserved patterns for Ig folds (SEQ ID NOs:8 and 10) using the SMART program, and based on their length, sequence similarity and secondary structure analysis, FAM was found to be comprised of two C2-type immunoglobulin domains (amino acids 41 to 116 and 144 to 219 of SEQ ID NO:3; SEQ ID NOs:9 and 11, respectively), as shown in FIGS. 4A and 4B. Localization of the C2 Ig domains within the structure of FAM is illustrated in the schematic model shown in FIG. 5.

EXAMPLE V

Search for Homologous cDNA and Protein Sequences

Comparisons of the FAM cDNA sequence against all known sequences in the GenBank Database and a literature search revealed homology of FAM to the recently cloned murine protein, junctional adhesion molecule (JAM) and to an antigen recognized by the A33 monoclonal antibody (FIG. 6). FAM appears to be a human homolog of murine JAM, which was shown to be localized at intracellular junctions of mouse endothelial and epithelial cells (Martin-Padura et al. 1998). The A33 antigen is a transmembrane glycoprotein expressed in gastrointestinal epithelium and in 95% of human colon cancers (Welt et al. 1990; Heath et al. 1997; Moritz et al. 1998). As shown in FIG. 6, a comparison of the amino acid sequences of the FAM (SEQ ID NO:3), JAM (SEQ ID NO:12) and A33 (SEQ ID NO:13) indicates that they contain a single transmembrane domain and two Ig folds. However, the two Ig domains of FAM are both of the C-2 type, whereas the first Ig domain of the A33 and JAM proteins have been categorized as V-type by the authors (Martin-Padura et al. 1998; Heath et al. 1997; Moritz et al. 1998).

EXAMPLE VI

Cellular Distribution of the FAM Molecule.

Figures 7E, 7F, 7G, 7H:
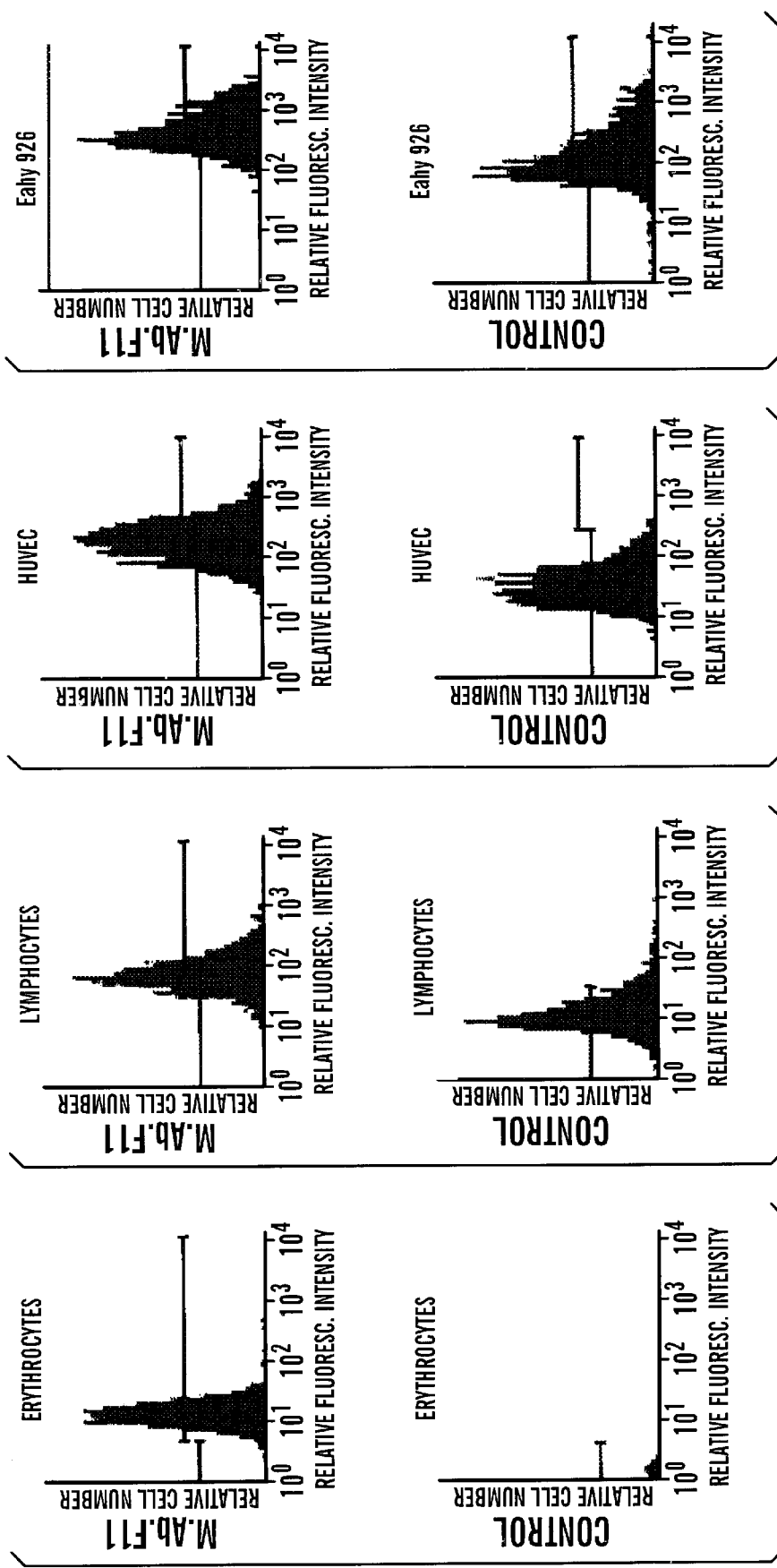
Figure 7I:
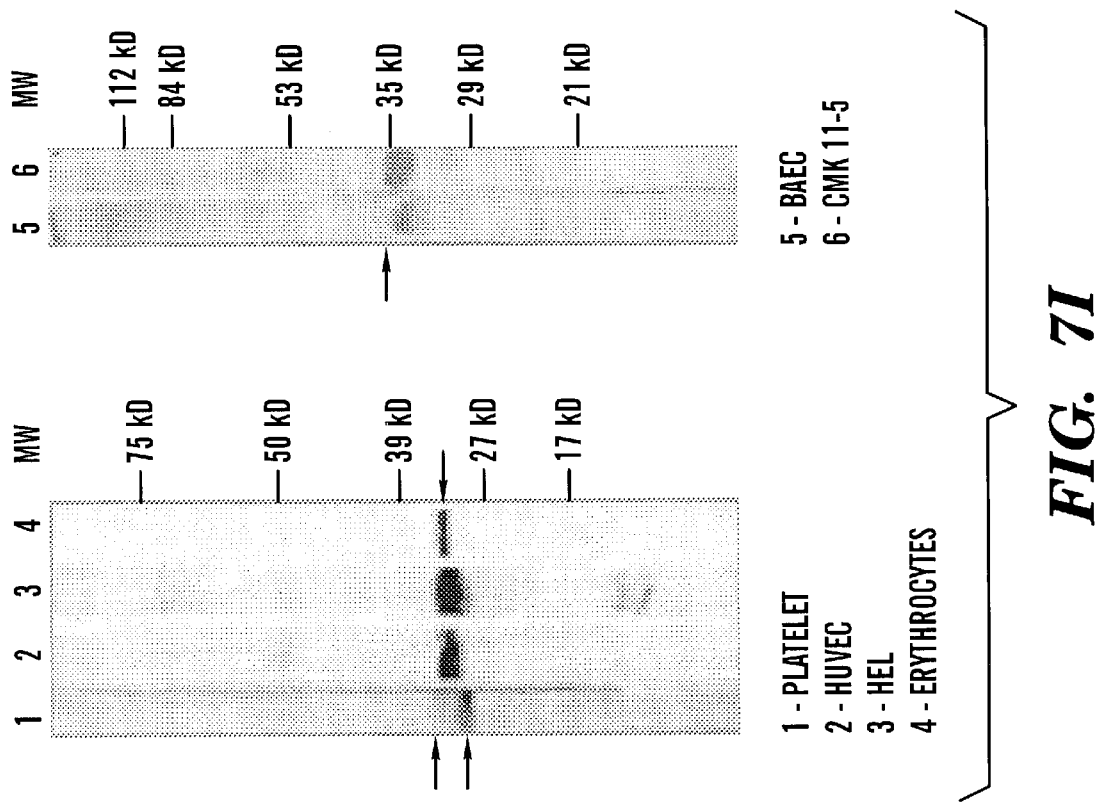
FIG. 7I illustrates the cellular distribution of FAM as determined by immunoblotting. Expression of the FAM in platelets (lane 1), endothelial cells HUVEC (lane 2), HEL cells (lane 3), human erythrocytes (lane 4), endothelial BAEC (lane 5) and CMK 11–15 cells (lane 6) is shown. Proteins were separated on 5–15% polyacrylamide gel (lanes 1–4) or by use of 12% SDS-PAGE (lanes 5–6). Immunoblotting was performed using M.Ab.F11 (4 µg/ml)

Fluorescence flow cytometry and immunoblotting procedures using M.Ab.F11 were used to examine the expression of FAM in various hematopoietic cells and cell lines. As shown in FIGS. 7A–7H, significant FAM was detected in parent CMK cells and subclones CMK6 and CMK11-5, HEL, K562, HUVEC, and the human endothelial hybrid cell line, Eahy 926, and erythrocytes and lymphocytes. Consistent with these observations was the identification of several glycosylated forms of FAM by immunoblotting. As shown in FIG. 7I, FAM was detected as a 32/35 kDa duplex in platelets, a single protein band of 35 kDa in red cells, and a broad protein band of 33/36 kDa in HUVEC and bovine aortic endothelial, K562 cells and human lymphocytes (data not shown).

EXAMPLE VII

Identification of FAM Antibodies in the Circulation of Patients

Figure 8:
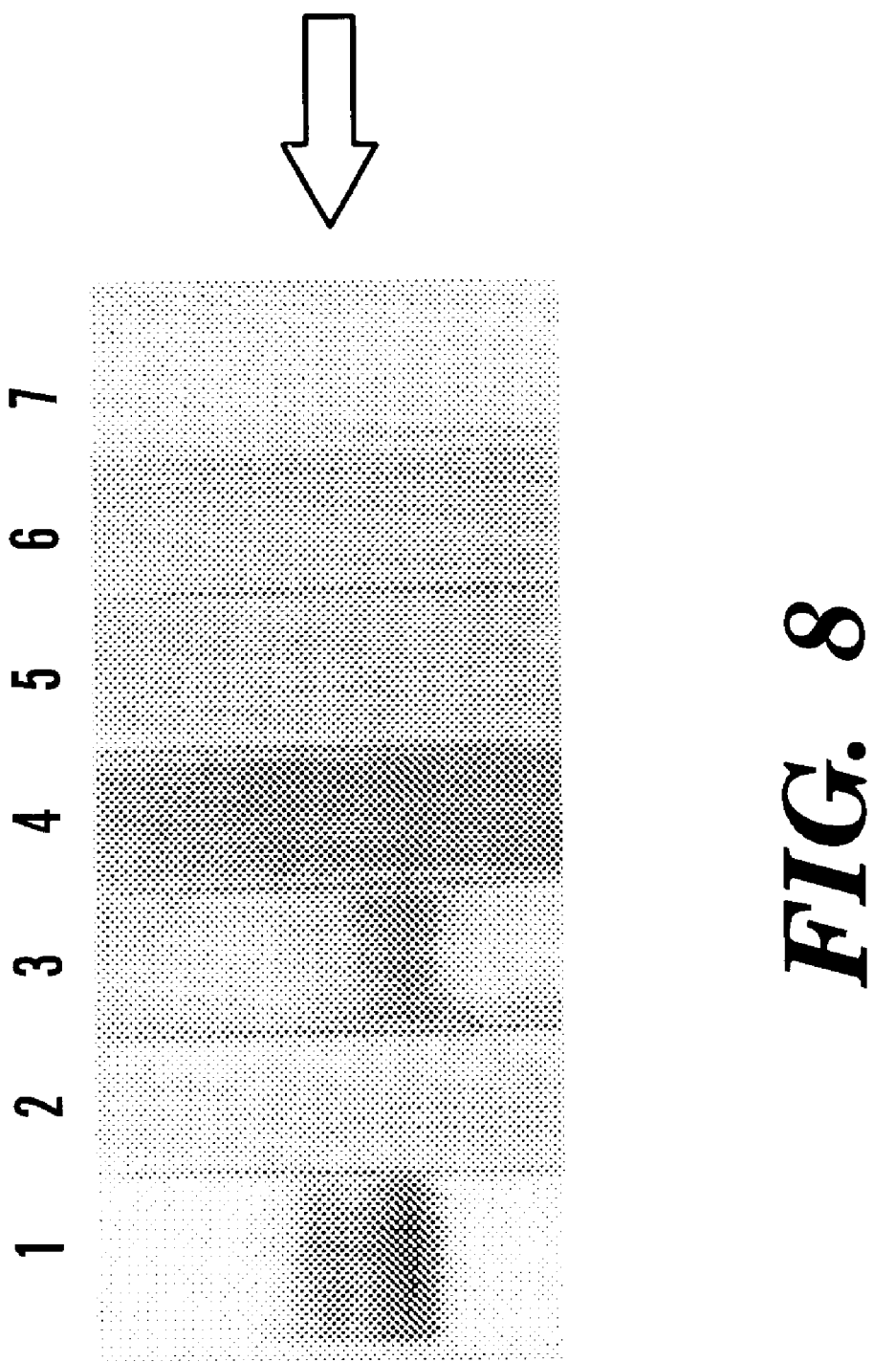
FIG. 8 illustrates the identification of FAM antibodies in the circulation of thrombocytopenic and renal disorder patients. FAM (5mg applied/lane), was purified from platelet plasma membranes using the affinity chromatographic procedures previously described (Kornecki et al. 1990; Naik et al. 1995) and resolved by SDS-PAGE. Immunoblotting was performed using the following antibodies: Lane 1, incubation with monoclonal antibody M.Ab.F11 (4 mg/ml); Lane 2, control, incubation with only 2° antibody, rabbit anti-mouse Ig; Lane 3, incubation with purified Ig fraction obtained from the serum of a thrombocytopenic patient (25 mg/ml); Lane 4, incubation with plasma obtained from a renal disorder patient, Lanes 5 and 6, incubation with plasmas obtained from two separate healthy donors and used for immunoblotting, Lane 7, control using 20 antibody, rabbit anti-human Ig.

FIG. 8 demonstrates the presence of FAM antibodies in the circulation of a thrombocytopenic patient (lane 3) and a renal disorder patient (lane 4). As shown in Lane 1, the murine monoclonal M.Ab.F11 detected both of the 32/35 kDa proteins in control platelet proteins. In comparison to M.Ab.F11, it appears that only the 32 kDa form of FAM could be detected by antibodies obtained from a thrombocytopenic patient (lane 3). Antibodies obtained from a renal disorder patient appear to detect both the 35 kDa as well as the 32 kDa forms (lane 4). In contrast, the plasmas of normal, healthy donors did not contain FAM antibodies, evidenced by a complete lack of FAM-labeling by normal plasma in lanes 5–7.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Properties of the FAM obtained by analysis of its amino acid composition deduced from cDNA sequence.

| Properties | Amino Acids | |
| --- | --- | --- |
| Molecular Weight | 29,682 kDa | |
| Isoelectric point | 6.72 | |
| Transmembrane helices | 12–29 | inside→outside |
|  | 239–258 | outside→inside |
| The cleavable N-term signal sequence | 1–27 | |
| The cytoplasmic tail | 255–299 | |
| N-glycosylation site | Asn-185 | |
| cAMP-/or cGMP-dependent protein kinase phosphorylation site | Thr-273 | |
| PKC phosphorylation sites | Ser-57 | Thr-269 |
|  | Thr-69 | Ser-274 |
|  | Thr-95 | Ser-275 |
|  | Ser-179 | Ser-284 |
| Casein kinase II phosphorylation sites | Ser-34 | Ser-154 |
|  | Ser-82 | Thr-193 |
|  | Thr-100 | Ser-203 |
|  | Ser-118 | Ser-287 |
|  | Thr-152 | |
| Tyrosines in the cytopl. tail | Tyr-260 | Tyr-279 |

Reference

Bachelot et al. (1990) Eur. J. Biochem. 190:177–183
Bause (1983) Biochem. J. 209:331–336
Bjellqvist et al. (1993) Electrophoresis 14:1023–1031
Bjellqvist et al. (1994) Electrophoresis 15:529–539
Bork et al. (1994) J. Mol. Biol. 242:309–302
Boucheix et al. (1983) FEBS 161:289–295
Boucheix et al. (1991) J Biol Chem 266:117–122
Brummendorf and Rathjen (1995) Protein Profile 2:963–1108
Capecchi (1980) Cell 22:479–488
Chomczynski and Sacchi (1987) Anal. Biochem. 162:156–159
Chrisey et al. (1991) Antisense Research and Development 1(1):57–63
Christoffersen and Marr (1995) J.J., Journal of Medicinal Chemistry 38(12):2023–2037
Coller et al. (1983) Blood 61:99–110
Coller et al. (1986) Blood 68:783–786
Cosgrove et al. (1988) Immunol Cell Biol 66:69–77
Duncan and Rosse (1986) Brit J Haematol 64:331–338
Gavel and von Heijne (1990) Protein Eng. 3:433–442
Glass and Smith (1983) J. Biol. Chem. 258:14797–14803
Glass et al. (1986) J. Biol. Chem. 261:2987–2993
Gorman et al. (1985) Nouv Fev Fr Hematol 27: 255–259
Han et al. (1991) Proc Natl Acad Sci USA 88:4313–4317
Handa et al. (1986) J Biol Chem 261:12579–12585
Heath et al. (1997) Proc. Natl. Acad. Sci. USA 94:469–474
Higashihara et al. (1985) Blood 65:382–391
Innis et al. (1990) PCR Protocols, Academic Press, San Diego, Calif.
Jennings et al. (1990) J. Biol. Chem. 265:3815–3822
Jones et al. (1982) Leuk Res 6:449–464
Karplus et al. (1997) Proteins. Suppl 1:134–139
Kersey et al. (1981) J Exp Med 153:726–731
Kishimoto et al. (1985) J. Biol. Chem. 260:12492–12499
Klein et al. (1987) Nature 327:70–73
Komada et al. (1983) Leuk Res 7:499–507
Kornecki et al. (1984) Thrombosis Research 34:35–49
Kornecki et al. (1990) J Biol Chem 265:10042–10048
Kornecki et al. (1995) Leucocyte Typing V (ed. Schlossman S F et al.), Oxford University Press, Oxford, pp. 1241–1243
Kozak (1987a) Nucl. Acid Res. 15:8125–8148
Kozak (1987b) J. Mol. Biol. 196:947–950
Kyte and Doolittle (1982) J. Mol. Biol. 157:105–132
Lanza et al. (1991) J Biol Chem 266:10638–10645
Mannino and Gould-Fogerite (1988) BioTechniques 6:682–690
Martin-Padura et al. (1998) J. Cell. Biol. 142:117–127
Miletich and Broze (1990) J. Biol. Chem. 265:11397–11404
Miller (1989) Bioessays 11:91–95
Modderman et al. (1988) Thromb Haemost 60:68–74
Morel et al. (1989) Brit J Haematol 71:57–63
Naik et al. (1995) Biochem. J. 310:155–162
Needleman and Wunsch (1970) J Mol Biol 48:443
Nielsen et al. (1997) Protein Engineering 10:1–6
Pearson and Lipman (1988) Proc Natl Acad Sci USA 85:2444
Peters et al. (1986) Brit Med J 293:1525
Pinna (1990) Biochim. Biophys. Acta 1054:267–284
Raucher et al. (1980) Tetrahedron. Lett. 21:14061
Rossi et al. (1992) AIDS Research and Human Retroviruses 8(2):183–189
Rossi (1995) British Medical Bulletin 51(1):217–225
Ryu et al. (1989) FASEB J 3:A312
Sambrook et al. (1989) Molecular Cloning: A Laboratory Manual. 2nd Ed., Cold Spring Harbor Laboratory Press, Cold Spring Harbor, N.Y.
Sarver et al. (1990) Science 247:1222–1225
Schultz et al. (1998) Proc. Natl. Acad. Sci. USA. 95:5857–5864

Schwoch and Passow (1973) Mol. & Cell. Bioch. 2:197–218
Scott et al. (1989) J Biol Chem 264:13475–13482
Shigekawa and Dower (1988) BioTechniques 6:742–751
Singer (1990) Ann. Rev. Cell Biol. 6:247–296
Smith and Waterman (1981) Adv Appl Math 2:482
Thiagarajan et al. (1983) Amer J Hematol 14:255–269
Wang et al. (1995) Biochem. J. 311:401–406
Wann et al. (1981) JOC 46:257
Welt et al. (1990) J. Clin. Oncol. 8:1894–1906
Williams and Barclay (1988) Ann. Rev. Immunol. 6:381–405
Williams et al. (1989) Cold Spring Harbor Symposia on Quantitative Biology. 54 Pt 2:637–647
Woodget et al. (1986) Eur. J. Biochem. 161:177–184
Worthington et al. (1990) Br J Haematol 74:216–222
Yanabu et al. (1991) Brit J Haematol 78:87–93

What is claimed is:

1. An isolated nucleic acid molecule encoding a human platelet F11 receptor, wherein said nucleic acid molecule encodes an amino acid sequence selected from the group consisting of SEQ ID NO:3, amino acid residues 28–299 of SEQ ID NO:3, SEQ ID NO:4, and amino acid residues 28–193 of SEQ ID NO:4.

2. The isolated nucleic acid molecule of claim 1 wherein said nucleic acid is deoxyribonucleic acid.

3. The isolated nucleic acid molecule of claim 2 wherein said deoxyribonucleic acid is cDNA.

4. The isolated nucleic acid molecule of claim 3 wherein said nucleic acid molecule has a nucleotide sequence selected from the group consisting of SEQ ID NO:1, nucleotides 16–912 of SEQ ID NO:1, nucleotides 97–912 of SEQ ID NO:1, SEQ ID NO:2, nucleotides 16–594 of SEQ ID NO:2, and nucleotides 97–594 of SEQ ID NO:2.

5. The isolated nucleic acid molecule of claim 1 wherein said nucleic acid is ribonucleic acid.

6. The isolated nucleic acid molecule of claim 5 wherein said ribonucleic acid is mRNA.

7. A cell comprising the nucleic acid molecule of claim 1.

8. An expression vector comprising the nucleic acid molecule of claim 1.

9. The expression vector of claim 8 wherein said expression vector is selected from the group consisting of a plasmid and a virus.

10. A cell comprising the expression vector of claim 8.

11. A method of increasing expression of a human platelet F11 receptor in a host cell, said method comprising:

introducing the nucleic acid molecule of claim 1 into the cell; and allowing said cell to express said nucleic acid molecule resulting in the production of said human platelet F11 receptor in said cell.

* * * * *

SEQUENCE LISTING

<160> NUMBER OF SEQ ID NOS: 27

<210> SEQ ID NO 1
<211> LENGTH: 1822
<212> TYPE: DNA
<213> ORGANISM: Homo sapiens

<400> SEQUENCE: 1

```
agtggcctga tcgcgatggg gacaaaggcg caagtcgaga ggaaactgtt gtgcctcttc    60
atattggcga tcctgttgtg ctccctggca ttgggcagtg ttacagtgca ctcttctgaa   120
cctgaagtca gaattcctga gaataatcct gtgaagttgt cctgtgccta ctcgggcttt   180
tcttctcccc gtgtggagtg gaagtttgac caaggagaca ccaccagact cgtttgctat   240
aataacaaga tcacagcttc ctatgaggac cgggtgacct tcttgccaac tggtatcacc   300
ttcaagtccg tgacacggga agacactggg acatacactt gtatggtctc tgaggaaggc   360
ggcaacagct atgggaggt caaggtcaag ctcatcgtgc ttgtgcctcc atccaagcct   420
acagttaaca tcccctcctc tgccaccatt gggaaccggg cagtgctgac atgctcagaa   480
caagatggtt ccccaccttc tgaatacacc tggttcaaag atgggatagt gatgcctacg   540
aatcccaaaa gcacccgtgc cttcagcaac tcttcctatg tcctgaatcc cacaacagga   600
gagctggtct ttgatcccct gtcagcctct gatactggag aatacagctg tgaggcacgg   660
aatgggtatg ggacacccat gacttcaaat gctgtgcgca tggaagctgt ggagcggaat   720
gtggggtca tcgtggcagc cgtccttgta accctgattc tcctgggaat cttggttttt   780
ggcatctggt ttgcctatag ccgaggccac tttgacagaa caaagaaagg gacttcgagt   840
aagaaggtga tttacagcca gcctagtgcc cgaagtgaag gagaattcaa acagacctcg   900
tcattcctgg tgtgagcctg gtcggctcac cgcctatcat ctgcatttgc cttactcagg   960
tgctaccgga ctctggcccc tgatgtctgt agtttcacag gatgccttat ttgtcttcta  1020
cacccccacag ggcccctac ttcttcggat gtgtttttaa taatgtcagc tatgtgcccc  1080
atcctccttc atgccctccc tcccttcct accactgctg agtggcctgg aacttgttta  1140
aagtgtttat tcctcatttc tttgagggat caggaaggaa tcctgggtat gccattgact  1200
tcccttctaa gtagacagca aaaatggcgg gggtcgcagg aatctgcact caactgccca  1260
cctggctggc agggatcttt gaataggtat cttgagcttg gttctgggct cttcccttgt  1320
gtactgacga ccagggccag ctgttctaga gcgggaatta gaggctagag cggctgaaat  1380
ggttgtttgg tgatgacact ggggtccttc catctctggg gcccactctc ttctgtcttc  1440
ccatgggaag tgccactggg atccctctgc cctgtcctcc tgaatacaag ctgactgaca  1500
ttgactgtgt ctgtggaaaa tgggagctct tgttgtggag agcatagtaa attttcagag  1560
aacttgaagc caaaaggatt taaaaccgct gctctaaaga aaagaaaact ggaggctggg  1620
cgcagtggct cacgcctata atcccagagg ctgaggcagg cggatcacct gaggtcagga  1680
```

-continued

```
gttcaggatc agcctgacca acatggagaa accctgctgg aaatacaaag ttagccaggc    1740
atggtggtgc atgcctgtag tcccagctgc tcaggagcct ggcaacaaga gcaaaactcc    1800
agctcaaaaa aaaaaaaaaa aa                                              1822
```

<210> SEQ ID NO 2
<211> LENGTH: 721
<212> TYPE: DNA
<213> ORGANISM: Homo sapiens

<400> SEQUENCE: 2

```
agtggcctga tcgcgatggg gacaaaggcg caagtcgaga ggaaactgtt gtgcctcttc     60
atattggcga tcctgttgtg ctccctggca ttgggcagtg ttacagtgca ctcttctgaa    120
cctgaagtca gaattcctga gaataatcct gtgaagttgt cctgtgccta ctcgggcttt    180
tcttctcccc gtgtggagtg gaagtttgac caaggagaca ccaccagact cgtttgctat    240
aataacaaga tcacagcttc ctatgaggac cgggtgacct tcttgccaac tggtatcacc    300
ttcaagtccg tgacacggga agacactggg acatacactt gtatggtctc tgaggaaggc    360
ggcaacagct atgggaggt caaggtcaag ctcatcgtgc ttgtgcctcc atccaagcct     420
acagttaaca tcccctcctc tgccaccatt gggaaccggg cagtgctgac atgctcagaa    480
caagatggtt ccccaccttc tgaatacacc tggttcaaag atgggatagt gacgcctata    540
atcccagagg ctgaggcagg cggatcacct gaggtcagga gttcaagatc agcctgacca    600
acatggagaa accctactaa aaatacaaag ttagccaggc atagtggtgc atgcctgtaa    660
tcccagctgc tcaggagcct ggcaacaaga gcaaaactcc agctcaaaaa aaaaaaaaaa    720
a                                                                     721
```

<210> SEQ ID NO 3
<211> LENGTH: 299
<212> TYPE: PRT
<213> ORGANISM: Homo sapiens

<400> SEQUENCE: 3

```
Met Gly Thr Lys Ala Gln Val Glu Arg Lys Leu Leu Cys Leu Phe Ile
  1               5                  10                  15

Leu Ala Ile Leu Leu Cys Ser Leu Ala Leu Gly Ser Val Thr Val His
                 20                  25                  30

Ser Ser Glu Pro Glu Val Arg Ile Pro Glu Asn Asn Pro Val Lys Leu
             35                  40                  45

Ser Cys Ala Tyr Ser Gly Phe Ser Ser Pro Arg Val Glu Trp Lys Phe
         50                  55                  60

Asp Gln Gly Asp Thr Thr Arg Leu Val Cys Tyr Asn Asn Lys Ile Thr
 65                  70                  75                  80

Ala Ser Tyr Glu Asp Arg Val Thr Phe Leu Pro Thr Gly Ile Thr Phe
                 85                  90                  95

Lys Ser Val Thr Arg Glu Asp Thr Gly Thr Tyr Thr Cys Met Val Ser
            100                 105                 110

Glu Glu Gly Gly Asn Ser Tyr Gly Glu Val Lys Val Lys Leu Ile Val
        115                 120                 125

Leu Val Pro Pro Ser Lys Pro Thr Val Asn Ile Pro Ser Ser Ala Thr
    130                 135                 140

Ile Gly Asn Arg Ala Val Leu Thr Cys Ser Glu Gln Asp Gly Ser Pro
145                 150                 155                 160

Pro Ser Glu Tyr Thr Trp Phe Lys Asp Gly Ile Val Met Pro Thr Asn
```

```
                        165                 170                 175
Pro Lys Ser Thr Arg Ala Phe Ser Asn Ser Ser Tyr Val Leu Asn Pro
                180                 185                 190

Thr Thr Gly Glu Leu Val Phe Asp Pro Leu Ser Ala Ser Asp Thr Gly
            195                 200                 205

Glu Tyr Ser Cys Glu Ala Arg Asn Gly Tyr Gly Thr Pro Met Thr Ser
        210                 215                 220

Asn Ala Val Arg Met Glu Ala Val Glu Arg Asn Val Gly Val Ile Val
225                 230                 235                 240

Ala Ala Val Leu Val Thr Leu Ile Leu Leu Gly Ile Leu Val Phe Gly
                245                 250                 255

Ile Trp Phe Ala Tyr Ser Arg Gly His Phe Asp Arg Thr Lys Lys Gly
            260                 265                 270

Thr Ser Ser Lys Lys Val Ile Tyr Ser Gln Pro Ser Ala Arg Ser Glu
        275                 280                 285

Gly Glu Phe Lys Gln Thr Ser Ser Phe Leu Val
290                 295
```

<210> SEQ ID NO 4
<211> LENGTH: 193
<212> TYPE: PRT
<213> ORGANISM: Homo sapiens

<400> SEQUENCE: 4

```
Met Gly Thr Lys Ala Gln Val Glu Arg Lys Leu Leu Cys Leu Phe Ile
1               5                   10                  15

Leu Ala Ile Leu Leu Cys Ser Leu Ala Leu Gly Ser Val Thr Val His
                20                  25                  30

Ser Ser Glu Pro Glu Val Arg Ile Pro Glu Asn Asn Pro Val Lys Leu
            35                  40                  45

Ser Cys Ala Tyr Ser Gly Phe Ser Ser Pro Arg Val Glu Trp Lys Phe
        50                  55                  60

Asp Gln Gly Asp Thr Thr Arg Leu Val Cys Tyr Asn Asn Lys Ile Thr
65                  70                  75                  80

Ala Ser Tyr Glu Asp Arg Val Thr Phe Leu Pro Thr Gly Ile Thr Phe
                85                  90                  95

Lys Ser Val Thr Arg Glu Asp Thr Gly Thr Tyr Thr Cys Met Val Ser
            100                 105                 110

Glu Glu Gly Gly Asn Ser Tyr Gly Glu Val Lys Val Lys Leu Ile Val
        115                 120                 125

Leu Val Pro Pro Ser Lys Pro Thr Val Asn Ile Pro Ser Ser Ala Thr
130                 135                 140

Ile Gly Asn Arg Ala Val Leu Thr Cys Ser Glu Gln Asp Gly Ser Pro
145                 150                 155                 160

Pro Ser Glu Tyr Thr Trp Phe Lys Asp Gly Ile Val Thr Pro Ile Ile
                165                 170                 175

Pro Glu Ala Glu Ala Gly Gly Ser Pro Glu Val Arg Ser Ser Arg Ser
            180                 185                 190

Ala
```

<210> SEQ ID NO 5
<211> LENGTH: 22
<212> TYPE: PRT
<213> ORGANISM: Homo sapiens

<400> SEQUENCE: 5

Ser Val Thr Val His Ser Ser Glu Pro Glu Val Arg Ile Pro Glu Asn
1               5                   10                  15

Asn Pro Val Lys Leu Ser
            20

<210> SEQ ID NO 6
<211> LENGTH: 42
<212> TYPE: PRT
<213> ORGANISM: Homo sapiens

<400> SEQUENCE: 6

Trp Lys Phe Asp Gln Gly Asp Thr Thr Arg Leu Val Cys Tyr Asn Asn
1               5                   10                  15

Lys Ile Thr Ala Ser Tyr Glu Asp Arg Val Thr Phe Leu Pro Thr Gly
            20                  25                  30

Ile Thr Phe Lys Ser Val Thr Arg Glu Asp
            35                  40

<210> SEQ ID NO 7
<211> LENGTH: 8
<212> TYPE: PRT
<213> ORGANISM: Homo sapiens

<400> SEQUENCE: 7

Lys Val Lys Leu Ile Val Leu Val
1               5

<210> SEQ ID NO 8
<211> LENGTH: 63
<212> TYPE: PRT
<213> ORGANISM: Homo sapiens

<400> SEQUENCE: 8

Leu Glu Gly Gln Ser Val Thr Leu Thr Cys Pro Ala Ser Gly Asp Pro
1               5                   10                  15

Val Pro Asn Ile Thr Trp Leu Lys Asp Gly Lys Pro Leu Pro Glu Ser
            20                  25                  30

Arg Leu Val Ala Ser Gly Ser Thr Leu Thr Ile Lys Asn Val Ser Leu
            35                  40                  45

Glu Asp Ser Gly Leu Tyr Thr Cys Val Ala Arg Asn Ser Val Gly
        50                  55                  60

<210> SEQ ID NO 9
<211> LENGTH: 76
<212> TYPE: PRT
<213> ORGANISM: Homo sapiens

<400> SEQUENCE: 9

Pro Glu Asn Asn Pro Val Lys Leu Ser Cys Ala Tyr Ser Gly Phe Ser
1               5                   10                  15

Ser Pro Arg Val Glu Trp Lys Phe Asp Gln Gly Asp Thr Thr Arg Leu
            20                  25                  30

Val Cys Tyr Asn Asn Lys Ile Thr Ala Ser Tyr Glu Asp Arg Val Thr
            35                  40                  45

Phe Leu Pro Thr Gly Ile Thr Phe Lys Ser Val Thr Arg Glu Asp Thr
            50                  55                  60

Gly Thr Tyr Thr Cys Met Val Ser Glu Glu Gly Gly
65                  70                  75

```
<210> SEQ ID NO 10
<211> LENGTH: 63
<212> TYPE: PRT
<213> ORGANISM: Homo sapiens

<400> SEQUENCE: 10

Leu Glu Gly Gln Ser Val Thr Leu Thr Cys Pro Ala Ser Gly Asp Pro
 1               5                  10                  15

Val Pro Asn Ile Thr Trp Leu Lys Asp Gly Lys Pro Leu Pro Glu Ser
            20                  25                  30

Arg Leu Val Ala Ser Gly Ser Thr Leu Thr Ile Lys Asn Val Ser Leu
        35                  40                  45

Glu Asp Ser Gly Leu Tyr Thr Cys Val Ala Arg Asn Ser Val Gly
    50                  55                  60

<210> SEQ ID NO 11
<211> LENGTH: 76
<212> TYPE: PRT
<213> ORGANISM: Homo sapiens

<400> SEQUENCE: 11

Thr Ile Gly Asn Arg Ala Val Leu Thr Cys Ser Glu Gln Asp Gly Ser
 1               5                  10                  15

Pro Pro Ser Glu Tyr Thr Trp Phe Lys Asp Gly Ile Val Met Pro Thr
            20                  25                  30

Asn Pro Lys Ser Thr Arg Ala Phe Ser Asn Ser Ser Tyr Val Leu Asn
        35                  40                  45

Pro Thr Thr Gly Glu Leu Val Phe Asp Pro Leu Ser Ala Ser Asp Thr
    50                  55                  60

Gly Glu Tyr Ser Cys Glu Ala Arg Asn Gly Tyr Gly
65                  70                  75

<210> SEQ ID NO 12
<211> LENGTH: 300
<212> TYPE: PRT
<213> ORGANISM: Mus musculus

<400> SEQUENCE: 12

Met Gly Thr Glu Gly Lys Ala Gly Arg Lys Leu Leu Phe Leu Phe Thr
 1               5                  10                  15

Ser Met Ile Leu Gly Ser Leu Val Gln Gly Lys Gly Ser Val Tyr Thr
            20                  25                  30

Ala Gln Ser Asp Val Gln Val Pro Glu Asn Glu Ser Ile Lys Leu Thr
        35                  40                  45

Cys Thr Tyr Ser Gly Phe Ser Ser Pro Arg Val Glu Trp Lys Phe Val
    50                  55                  60

Gln Gly Ser Thr Thr Ala Leu Val Cys Tyr Asn Ser Gln Ile Thr Ala
65                  70                  75                  80

Pro Tyr Ala Asp Arg Val Thr Phe Ser Ser Ser Gly Ile Thr Phe Ser
                85                  90                  95

Ser Val Thr Arg Lys Asp Asn Gly Glu Tyr Thr Cys Met Val Ser Glu
            100                 105                 110

Glu Gly Gly Gln Asn Tyr Gly Glu Val Ser Ile His Leu Thr Val Leu
        115                 120                 125

Val Pro Pro Ser Lys Pro Thr Ile Ser Val Pro Ser Ser Val Thr Ile
    130                 135                 140

Gly Asn Arg Ala Val Leu Thr Cys Ser Glu His Asp Gly Ser Pro Pro
145                 150                 155                 160
```

```
Ser Glu Tyr Ser Trp Phe Lys Asp Gly Ile Ser Met Leu Thr Ala Asp
                165                 170                 175

Ala Lys Lys Thr Arg Ala Phe Met Asn Ser Ser Phe Thr Ile Asp Pro
            180                 185                 190

Lys Ser Gly Asp Leu Ile Phe Asp Pro Val Thr Ala Phe Asp Ser Gly
        195                 200                 205

Glu Tyr Tyr Cys Gln Ala Gln Asn Gly Tyr Gly Thr Ala Met Arg Ser
    210                 215                 220

Glu Ala Ala His Met Asp Ala Val Glu Leu Asn Val Gly Gly Ile Val
225                 230                 235                 240

Ala Ala Val Leu Val Thr Leu Ile Leu Leu Gly Leu Leu Ile Phe Gly
                245                 250                 255

Val Trp Phe Ala Tyr Ser Arg Gly Tyr Phe Glu Thr Thr Lys Lys Gly
                260                 265                 270

Thr Ala Pro Gly Lys Lys Val Ile Tyr Ser Gln Pro Ser Thr Arg Ser
            275                 280                 285

Glu Gly Glu Phe Lys Gln Thr Ser Ser Phe Leu Val
        290                 295                 300

<210> SEQ ID NO 13
<211> LENGTH: 316
<212> TYPE: PRT
<213> ORGANISM: Homo sapiens

<400> SEQUENCE: 13

Met Val Gly Lys Met Trp Pro Val Leu Trp Thr Leu Cys Ala Val Arg
  1               5                  10                  15

Val Thr Val Asp Ala Ile Ser Val Glu Thr Pro Gln Asp Val Leu Arg
                 20                  25                  30

Ala Ser Gln Gly Lys Ser Val Thr Leu Pro Cys Thr Tyr His Thr Ser
             35                  40                  45

Thr Ser Ser Arg Glu Gly Leu Ile Gln Trp Asp Lys Thr His Thr Glu
         50                  55                  60

Arg Val Val Ile Trp Pro Phe Ser Asn Lys Asn Tyr Ile His Gly Glu
 65                  70                  75                  80

Leu Tyr Lys Asn Arg Val Ser Ile Ser Asn Asn Ala Glu Gln Ser Asp
                 85                  90                  95

Ala Ser Ile Thr Ile Asp Gln Leu Thr Met Ala Asp Asn Gly Thr Tyr
            100                 105                 110

Glu Cys Ser Val Ser Leu Met Ser Asp Leu Glu Gly Asn Thr Lys Ser
        115                 120                 125

Arg Val Arg Leu Leu Val Leu Val Pro Pro Ser Lys Pro Glu Cys Gly
    130                 135                 140

Ile Glu Gly Glu Thr Ile Ile Gly Asn Asn Ile Gln Leu Thr Cys Gln
145                 150                 155                 160

Ser Lys Glu Gly Ser Pro Thr Pro Gln Tyr Ser Trp Lys Arg Tyr Asn
                165                 170                 175

Ile Leu Asn Gln Glu Gln Pro Leu Ala Gln Pro Ala Ser Gly Gln Pro
            180                 185                 190

Val Ser Leu Lys Asn Ile Ser Thr Asp Thr Ser Gly Tyr Tyr Ile Cys
        195                 200                 205

Thr Ser Ser Asn Glu Glu Gly Thr Gln Phe Cys Asn Ile Thr Val Ala
    210                 215                 220

Val Arg Ser Pro Ser Met Asn Val Ala Leu Tyr Val Gly Ile Ala Val
```

```
                225                 230                 235                 240
Gly Val Val Ala Ala Leu Ile Ile Ile Gly Ile Ile Tyr Cys Cys
                    245                 250                 255

Cys Cys Arg Gly Lys Asp Asp Asn Thr Glu Asp Lys Glu Asp Ala Arg
                260                 265                 270

Pro Asn Arg Glu Ala Tyr Glu Glu Pro Pro Glu Gln Leu Arg Glu Leu
            275                 280                 285

Ser Arg Glu Arg Glu Glu Asp Asp Tyr Arg Gln Glu Glu Gln Arg
    290                 295                 300

Ser Thr Gly Arg Glu Ser Pro Asp His Leu Asp Gln
305                 310                 315

<210> SEQ ID NO 14
<211> LENGTH: 26
<212> TYPE: PRT
<213> ORGANISM: Homo sapiens
<220> FEATURE:
<223> OTHER INFORMATION: residue 23 is a variable amino acid

<400> SEQUENCE: 14

Ser Val Thr Val His Ser Ser Glu Pro Glu Val Arg Ile Pro Glu Asn
1               5                   10                  15

Asn Pro Val Lys Leu Ser Xaa Ala Tyr Ser
            20                  25

<210> SEQ ID NO 15
<211> LENGTH: 42
<212> TYPE: PRT
<213> ORGANISM: Homo sapiens

<400> SEQUENCE: 15

Trp Lys Phe Asp Gln Gly Asp Thr Thr Arg Leu Val Glu Tyr Asn Asn
1               5                   10                  15

Lys Ile Thr Ala Ser Tyr Glu Asp Arg Val Thr Phe Leu Pro Thr Gly
            20                  25                  30

Ile Thr Phe Lys Ser Val Thr Arg Glu Asp
        35                  40

<210> SEQ ID NO 16
<211> LENGTH: 20
<212> TYPE: DNA
<213> ORGANISM: Homo sapiens

<400> SEQUENCE: 16
gartayaaya ayaarathac                                              20

<210> SEQ ID NO 17
<211> LENGTH: 20
<212> TYPE: DNA
<213> ORGANISM: Homo sapiens
<220> FEATURE:
<223> OTHER INFORMATION: nucleotides 6, 12 and 15 can be C, T, G or A

<400> SEQUENCE: 17
ttraangtda tnccngtagg                                              20

<210> SEQ ID NO 18
<211> LENGTH: 20
<212> TYPE: DNA
<213> ORGANISM: Homo sapiens
<220> FEATURE:
<223> OTHER INFORMATION: nucleotides 6, 12, and 15 can be C, T, G or A
```

<400> SEQUENCE: 18
ttraangtda tnccngtcgg                                                   20

<210> SEQ ID NO 19
<211> LENGTH: 20
<212> TYPE: DNA
<213> ORGANISM: Homo sapiens
<220> FEATURE:
<223> OTHER INFORMATION: nucleotides 6, 12 and 15 can be A, T, C or G

<400> SEQUENCE: 19
ttraangtda tnccngtggg                                                   20

<210> SEQ ID NO 20
<211> LENGTH: 20
<212> TYPE: DNA
<213> ORGANISM: Homo sapiens
<220> FEATURE:
<223> OTHER INFORMATION: nucleotides 6, 12 and 15 can be A, T, C or G

<400> SEQUENCE: 20
ttraangtda tnccngttgg                                                   20

<210> SEQ ID NO 21
<211> LENGTH: 20
<212> TYPE: DNA
<213> ORGANISM: Homo sapiens

<400> SEQUENCE: 21
agcttcctat gaggaccggg                                                   20

<210> SEQ ID NO 22
<211> LENGTH: 17
<212> TYPE: DNA
<213> ORGANISM: Homo sapiens

<400> SEQUENCE: 22
gtcacggact tgaaggt                                                      17

<210> SEQ ID NO 23
<211> LENGTH: 21
<212> TYPE: DNA
<213> ORGANISM: Homo sapiens

<400> SEQUENCE: 23
ggcaagaagg tcacccggtc c                                                 21

<210> SEQ ID NO 24
<211> LENGTH: 20
<212> TYPE: DNA
<213> ORGANISM: Homo sapiens
<220> FEATURE:
<223> OTHER INFORMATION: nucleotides 6, 12 and 15 can be A, T, C or G

<400> SEQUENCE: 24
ttraangtda tnccngttgg                                                   20

<210> SEQ ID NO 25
<211> LENGTH: 20
<212> TYPE: DNA
<213> ORGANISM: Homo sapiens

<400> SEQUENCE: 25

-continued

```
atctggtttg cctatagccg                                          20

<210> SEQ ID NO 26
<211> LENGTH: 20
<212> TYPE: DNA
<213> ORGANISM: Homo sapiens

<400> SEQUENCE: 26
ctctagcctc taattcccgc                                          20

<210> SEQ ID NO 27
<211> LENGTH: 20
<212> TYPE: DNA
<213> ORGANISM: Homo sapiens
<220> FEATURE:
<223> OTHER INFORMATION: nucleotides 6 and 12 can be A, T, C or G

<400> SEQUENCE: 27
ttraangtda tnccrgttgg                                          20
```